US008338423B2

(12) United States Patent
Pey Rodríguez et al.

(10) Patent No.: US 8,338,423 B2
(45) Date of Patent: Dec. 25, 2012

(54) COMPOSITIONS FOR THE TREATMENT OF HYPERPHENYLALANINEMIA

(75) Inventors: Ángel Pey Rodríguez, Zaragoza (ES); Aurora Martínez Ruiz, Zaragoza (ES); Javier Sancho Sanz, Zaragoza (ES); Nunilo Cremades Casasín, Zaragoza (ES); Adrián Velázquez Campoy, Zaragoza (ES); Ming Ying, Zaragoza (ES)

(73) Assignee: Universidad de Zaragoza, Zaragoza (ES)

( * ) Notice: Subject to any disclaimer, the term of this patent is extended or adjusted under 35 U.S.C. 154(b) by 15 days.

(21) Appl. No.: 12/666,828

(22) PCT Filed: Jun. 27, 2008

(86) PCT No.: PCT/EP2008/005294
§ 371 (c)(1),
(2), (4) Date: Jul. 22, 2010

(87) PCT Pub. No.: WO2009/000552
PCT Pub. Date: Dec. 31, 2008

(65) Prior Publication Data
US 2010/0286166 A1 Nov. 11, 2010

(30) Foreign Application Priority Data

Jun. 28, 2007 (EP) .................................. 07012682

(51) Int. Cl.
*A61K 31/50* (2006.01)
*C07D 239/70* (2006.01)
(52) U.S. Cl. ........................ 514/249; 544/253
(58) Field of Classification Search .................. 514/249; 544/253
See application file for complete search history.

(56) References Cited

U.S. PATENT DOCUMENTS 6,310,067 B1 * 10/2001 Ogata et al. ............. 514/253.09
6,838,461 B1 * 1/2005 Boettcher et al. ........ 514/254.09
2001/0011070 A1 8/2001 Georgi

FOREIGN PATENT DOCUMENTS

DE 19534602 4/1997
WO WO 9854190 12/1998
WO WO 2006060702 6/2006
WO WO 2006116355 11/2006

OTHER PUBLICATIONS

International Search Report of International PCT application No. PCT/EP2008/005294 mailed Dec. 4, 2008.
Arawaka et al., Biochim Biophys Acta, 2006,1764:11, 1677-1687.
Bernegger et al., Molecular Genetics and Metabolism, 2002, 77:4, 2002, 304-313.
Bhatnagar et al., Indian Journal of Experimental Biology, 1992, 30:7, 619-23.
Bjørgo et al., Eur. J. Biochem., 1988, 257:1, 1-10.
Blau et al., Mol Genet Metab, 2004, 82:2, 101-111.
Cannito et al., European Journal of Medicinal Chemistry, Editions Scientifique Elsevier, Paris, Fr, 1990, 25:8, 635-639.
Cansev et al., Aromatic Amino Acids in the Brain, in Handbook of Neurochemistry and Molecular Neurobiology, Lajtha, Ed., Springer-Verlag Berlin Heidelberg, 2007, Chapter 4, 60-87.
Cimmperman et al., Biophysical Journal, 2008, 95, 3222-3231.
Concolino et al., BMC Pediatrics, 2010, 10:32, 1-3.
Dergez et al., BMC Structural Biology, 2007, 7:41, 1-10, available from http://www.biomedcentral.com/1472-6807/7/41.
Ding et al., Gene Ther, 2006, 13:7, 587-593.
Døskeland et al., J. Biol. Chem., 1984, 259:18, 11242-11248.
Duval et al., Bioorganic & Medicinal Chemistry Letters, 2005, 15:7, 1885-1889.
Elzaouk, et al. J Biol Chem., 2003, 278:30, 28303-28311.
Erlandsen et al., Biochemistry, 2000, 39, 2208-2217.
Erlandsen et al., Proc Natl Acad Sci USA , 2004, 101:48, 16903-16908.
Gambol, J Pediatr Nurs, 2007, 22:2, 129-138.
Gamez et al., Mol Ther, 2005, 11:6, 986-989.
Gersting et al., American Journal of Human Genetics, 2008, 83, 5-17.
Gonzalez-Correa et al., Biosalud, 2009, 8, 132-142.
Harding et al., Gen Ther, 2006;13:5, 457-462.
Knappskog et al,. Eur. J. Biochem, 1996, 242, 813-821.
Knappskog et al., Hum. Mutat., 1996, 8, 236-246.
Koch et al., Molecular Genetics and Metabolism, 2003, 79, 110-113.
Leandro et al., Mini-Reviews in Medicinal Chemistry, 2008, 8:9, 901-911.
Martinez et al., Biochem. J., 1995, 306, 589-597.
Martinez-Cruz et al., Journal of Neuroscience Research, 2002, 69:4, 550-558.
Matalon et al., Pediatrics, 2003, 112(6Pt 2), 1570-1574.
Matulis et al., Biochemistry, 2005,44(13):5258-66.
Michals-Matalon et al., Journal of Nutrition, 2007, 137, 1564S-1567S.
Mukerjee et al., Indian Journal of Chemistry. Section B: Organic and Medicinal Chemistry, 1989, 28B, 391-396.
Nemazanyi et al., Chemistry of Heterocyclic Compounds (A Translation of Khimiya Geterotsiklicheskikh Soedinenii), 1992, 1, 86-88, XP002977626 ISSN: 0009-3122.
Pey et al., Mol Genet Metab, 2005, 2132:86 Suppl 1, S43-53.
Pey et al., Faseb J, 2006, 20:12, 2130-2132. Pey et al., Faseb J, 2006, 20: E1451-1464.
Pey et al., In: Blau N. ed., Advances in PKU and BH4, Advances in Phenylketonuria and Tetrahydrobiopterin, The Phenylanine Hydroxylase System, Heilbronn, SPS Verlagsgesellschaft MBH, 2006, 49-74.
Pey et al., Journal of Clinical Investigation, 2008, 118:8, 2858-2867.
Ranise et al., IL Farmaco, Aug.-Sep. 1997, 52:8-9, 547-555.
Rao et al., J. Chem. Pharm. Res., 2010, 2:2, 350-356.
Saify et al., Pakistan Journal of Pharmaceutical Sciences, 2000, 13:1, 29-32.
Sarkissian et al., PNAS, 2008, 105:52, 20894-20899.

(Continued)

*Primary Examiner* — Rei-tsang Shiao
(74) *Attorney, Agent, or Firm* — Merchant & Gould P.C.

(57) ABSTRACT

The present invention relates to the use of specific types of compounds acting as pharmacological chaperones having a stabilizing activity on the phenylalanine hydroxylase (PAH) enzyme for the prophylaxis and/or treatment of hyperphenylalaninemia (HPA) and phenylketonuria PKU) and diseases, disorders and conditions related thereto. Further, the present invention relates to pharmaceutical compositions containing the compounds according to the present invention as well as to methods of treatment of HPA, in particular, PKU and diseases, disorders and conditions related thereto.

10 Claims, 4 Drawing Sheets

OTHER PUBLICATIONS

Figure 1:
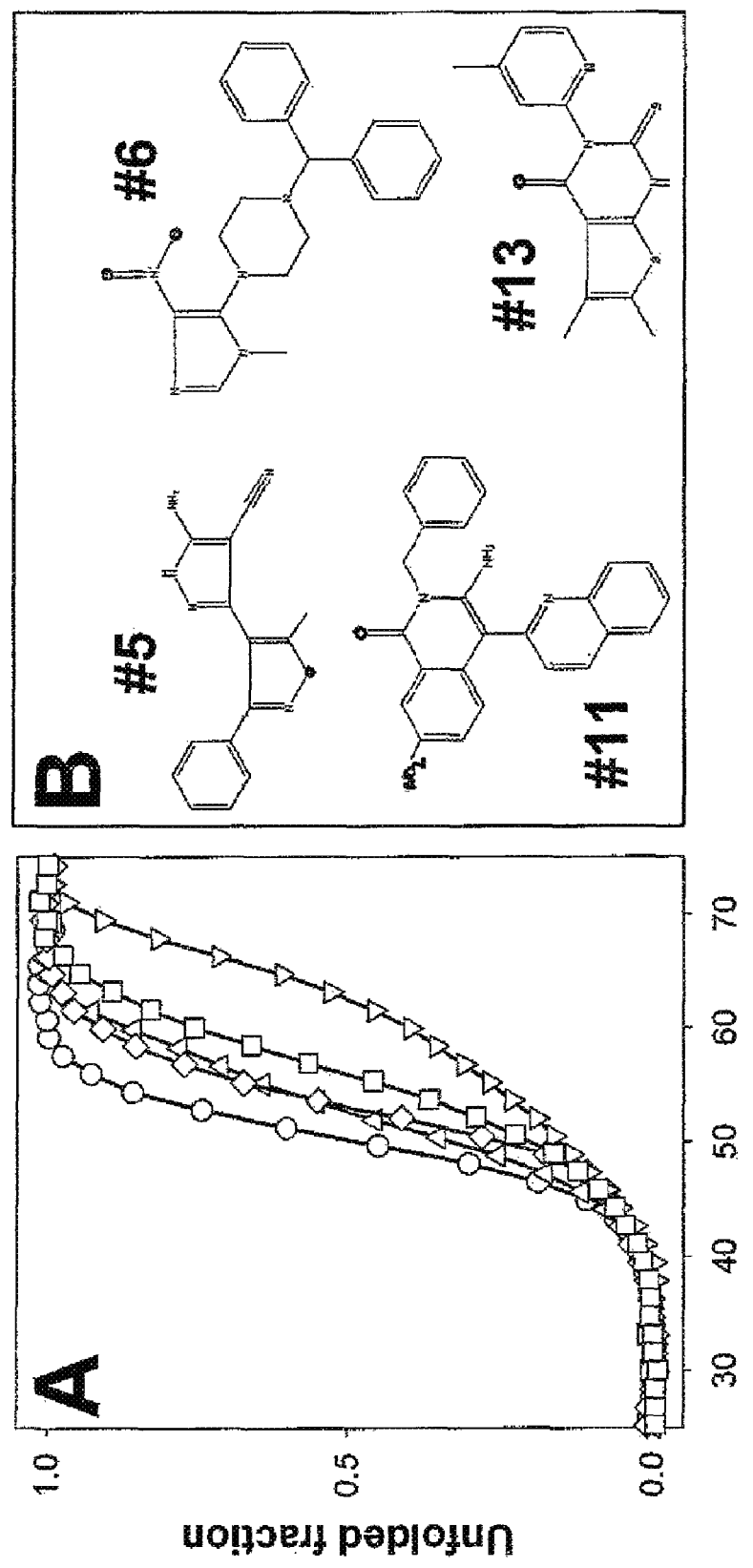

Scriver et al., Hyperphenylalaninemia: phenylalanine hydroxylase deficiency, In: Scriver, et al., Eds., The Metabolic and Molecular bases of Inherited Disease, 8$^{th}$ ed., New York: McGraw-Hill, 2001, 1667-1724.

Scriver, Hum Mutat, 2007, 28:9, 831-845.

Shalaby et al., Eds. McCulloch and Shalaby, Tailored Polymeric Materials for Controlled Delivery Systems, ACS Symposium Series, No. 709, 1998, Chapter 1, 2-22.

Thórólfsson et al., Biochemistry, 2002, 41:24, 7573-7585.

Vazquez et al., An Pediatr (Barc), 2006, 64:2, 146-152.

Wang et al., Mol Genet Metab, 2005, 86:1-2, 134-140.

Waters, Hum Mutat, 2003, 21:4, 357-369.

Waters, In: Blau N., ed., PKU and BH$_4$—Advances in Phenylketonuria and Tetrahydrobiopterin, Heilbronn: SPS Verlagsgesellschaft MBH, 2006, 277-310.

* cited by examiner

COMPOSITIONS FOR THE TREATMENT OF HYPERPHENYLALANINEMIA

This application is a National Stage Application of PCT/EP2008/005294, filed 27 Jun. 2008, which claims benefit of Serial No. 07012682.6, filed 28 Jun. 2007 in Europe and which application(s) are incorporated herein by reference. To the extent appropriate, a claim of priority is made to each of the above disclosed applications.

The present invention relates to the use of specific types of compounds acting as pharmacological chaperones having a stabilizing activity on the phenylalanine hydroxylase (PAH) enzyme for the prophylaxis and/or treatment of hyperphenylalaninemia (HPA) and phenylketonuria (PKU) and diseases, disorders and conditions related thereto. Further, the present invention relates to pharmaceutical compositions containing the compounds according to the present invention as well as to methods of treatment of HPA, in particular, PKU and diseases, disorders and conditions related thereto.

BACKGROUND ART

PKU is a human genetic disorder in which the body does not contain or contain in less amounts or less stable forms of the PAH enzyme, necessary to metabolize L-phenylalanine (L-Phe) to L-tyrosine (L-Tyr), but converts phenylalanine instead to phenylpyruvic acid by transamination, however, decarboxylation of L-Phe may also occur. That is, the body of the individual affected with said disease is not able to utilize the essential amino acid phenylalanine. Amino acids are the building of food since the individual does normally not produce the essential amino acids. In "classic phenylketonuria (PKU)" the enzyme that brakes down phenylalanine, PAH, is completely or nearly completely deficient, thus, no conversion to tyrosine takes place. Without this enzyme, phenylalanine and its breakdown chemicals from other enzymeroutes, accumulate in the blood and body tissues (Scriver C R, Kaufman S. Hyperphenylalaninemia: phenylalanine hydroxylase deficiency. In: Scriver C R, Beaudet A L, Valle D, Sly W S, eds. The Metabolic and Molecular bases of Inherited Disease. 8$^{th}$ ed. New York: McGraw-Hill, 2001: 1667-1724).

Further, the disease termed "hyperphenylalaninemia" (HPA) is used to describe the phenomenon of having elevated blood phenylalanine and, normally, include the specific form of PKU. About 98% of patients displaying HPA carry mutations in the phenylalanine hydroxylase (pah) gene, while the remaining 2% mainly affect enzymes involved in the synthesis or regeneration of PAH cofactor, tetrahydrobiopterin (BH$_4$) Scriver C R, Kaufman S. supra). In the following, HPA is used to include all type of diseases or disorders or conditions characterized in having an elevated phenylalanine level. PKU represents a special form of a disorder falling under the general term of HPA, where HPA is due to mutations in the pah gene.

As mentioned before, PKU and HPA are both caused by mutations in the pah gen, More than 60% of mutations associated to PKU are missense mutations (leading to a single amino acid substitution on the protein), and their main effects on PAH function seem to be associated to protein), and their main effects on PAH function seem to be associated to protein misfolding and increased turnover in vivo. Due to defects in converting the amino acid L-Phe to L-Tyr, L-Phe accumulates in the blood and is mainly excreted unchanged in the urine; some is transaminated to phenylpyruvic acid, which may be further metabolized to phenylacetic, phenyllactic and o-hydroxyphenylacetic acids; all are excreted in the urine (Scriver C R, Kaufman S. supra), Waters P J, Hum Mutat 2003; 21(4): 357-69; Scriver C R. The PAH gene, phenylketonuria, and a paradigm shift. Hum Mutat 2007.

PKU and most other causes of HPA are inherited in a recessive fashion (Scriver C R, Kaufman S. supra) This means, an affected person inherited two traits for the disorder. A person carrying only one mutation in the phenylalanine hydroxylase gene is called carrier for PKU, carriers do not have symptoms of the disorder. Classic PKU and the other causes of HPA affect about 1 of every 10,000 to 20,000 Caucasian or Oriental births. The incidence in African Americans is far less. These disorders are equally frequent in males and females.

The phenylalanine hydroxylase (PAH, phenylalanine 4-monooxigenase; EC1.14.16.1) is a non-heme iron dependent enzyme that catalyzes the hydroxylation of L-Phe to L-Tyr in the presence of tetrahydrobiopterin (BH4) and molecular dioxygen as cosubstrates, Fitzpatrick P F, Adv. Enzymol. Relat. Areas Mol. Biol. 2000; 74:235-294. In humans, PAH activity is mainly present in liver, and essential to provide L-Tyr for protein and neurotransmitters biosynthesis in liver, and essential to provide L-Tyr for protein and neurotransmitters biosynthesis, besides its involvement in energy metabolism. About 500 disease causing mutations have been described for the PAH gene, see e.g. the phenylalanine hydroxylase locus knowledgebase (PAHdb), at http:www.pandb.mcgill.cs. The molecular mechanisms responsible for the loss-of-function of PAH have pointed towards decreased conformational stability and, in some cases, kinetic abnormalities in the PAH enzyme in vitro and probably in vivo (Waters P J., Hum Mutat 2003; 21(4):357-69; Scriver C R., Hum Mutat 2007; Erlandsen H., et al., Proc Natl Acad Sci USA 2004; 101(48):16903-8).

Restriction on L-Phe intake by using artificial dietary formulations and early diagnosis through newborn screening tests have led to a remarkable success in preventing the major manifestations of the disease, including mental retardation. However, diet therapy has to be maintained "for life", it is relatively expensive and socially burdening and if not continued it may affect fetus development during pregnancy.

Typically, HPA is associated with mental retardation. Further, untreated children with classical PKU are normal at birth, but fail to attain earlier developmental milestones, develop microcephaly, and demonstrate progressive impairment of cerebral function. Hyperactivity, seizures, and severe mental retardation are major clinical problems later in life. Electroencephalographic abnormalities; "mousy" odor of skin, hair and urine (due to Phenylacetate accumulation); and a tendency to hypopigmentation and eczema complete the devastating clinical picture. With maternal PKU it is essential for women with PKU for the health of their children to maintain low phenylalanine levels before and during pregnancy. Otherwise, as a result, the children may develop congenital heart disease, growth retardation, microcephaly and mental retardation, (Gambol P J., J Pediatr Nurs 2007; 22(2):129-38

Currently, several different strategies to partially or totally substitute low-Phe diet and to treat PKU are investigation. BH$_4$ supplementation has been demonstrated to short and long term reduce-L-Phe levels and increase L-Phe tolerance in mils and severe PKU phenotypes, increasing the L-Phe oxidation in vivo, Blau N, Erlandsen H. Mol Genet Metad 2004; 82(2):101-11, probably due to a multifactor mechanisms involving stabilization of PAH mutant proteins against degradation/inactivation, Erlandsen H, et al., Proc Natl Acad Sci USA 2004; 101(48):16903-8. Large neutral amino acids (LNAA) supplementation is based on the reversal of the L-Phe induced inhibition of the LNAA transport across the blood-brain barrier by the L-type amino acid carrier, Matalon R, et al., Pediatrics 2003; 112(6Pt 2)1570-1574. The above approaches allow to facilitate the restrictive L-Phe diets. Additional approaches like gene-therapy and enzyme replacement therapy are aimed to completely eliminate L-Phe dietary restriciton and are currently the subject of intense research (Gamez A, et al., Mol ther 2005; 11(6):986-9 Wang L, et al., Mol Genet Metab 2005; 86(1-2):134-40; Harding C O, et Al., Ther 2006; 13(5):457-62; Ding Z, et al., Gene ther 2006; 13(7):587-93.

The object of the present invention is to provide a new approach to treat PKU and HPA and to provide new compounds useful therefore.

SUMMARY OF THE PRESENT INVENTION

The inventors have found new compounds for prophylaxis and/or treatment of HPA and PKU. The compounds are in stabilizing mutant PAH enzymes which are normally the cause of HPA or PKU. These so called pharmacological chaperones stabilize the PAH mutant proteins and, thus, allowing increased enzymatic activity of said enzyme in the body to process L-Phe to L-tyr. The compounds according to the present invention stabilize the enzymes without inhibiting significantly PAH activity upon ligand binding.

Thus, the present invention relates to the use of pharmacological chaperones having a stabilizing effect on the PAH and its physiologically compatible acid and base addiction salts and solvates in the preparation of a medicament for the prophylaxis and/or treatment of HPA, in particular, PKU and diseases, disorders and conditions resulting therefrom. Said pharmacological chaperones are selected from the group of a) a compound having the general formula I

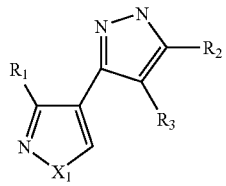

Wherein $X_1$ is $O_1 S_1 CR_A$ or $NR_B$ $R_A$ is selected from the group of H, halogen, OH, CN, $C_1$ to $C_6$ alkyl, substituted $C_1$ to $C_6$ alkoxy, substituted $C_1$ to $C_6$ alkoxy, $NH_2$, $C_1$ to $C_6$ aminoalkyl, substituted $C_1$ to $C_6$ aminoalkyl, aryl, substituted aryl, heterocyclic, or substituted $C_1$ to $C_6$ aminoalkyl, aryl, substituted aryl, heterocyclic, or substituted heterocyclic;

RB is selected from the group of H, $C_1$ to $C_6$ alkyl, substituted $C_1$ to $C_6$ alkyl, $C_1$ to $C_6$ alkoxy, substituted $C_1$ to $C_6$ alkoxy;

R1 is selected from H, OH, halogen, $NH_2$, $N(R_B)_2$, CN1, $C_1$ to $C_6$ alkyl, substituted $C_1$ to $C_6$ alkyl, a $C_1$ to $C_6$lkoxy, substituted $C_1$ to $C_6$alkoxy, $C_3$ to $C_6$ alkenyl, aryl, substituted aryl, heterocyclic, substituted heterocuclic, $COR_A$ wherein $R_A$ and $R_B$ are defined as above, and, in particular, a substituted benzene ring which may contain 1 or 2 heteroatoms selected from O, N and S, Containing the substituents A, B and C as shown below

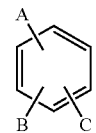

wherein A, B, and C are each independently selected from the group consisting of H, halogen, OH, CN, $C_1$ to $C_3$ alkyl, $C_1$ to $C_3$ substituted alkyl, $C_1$ to $C_3$ alkoxy, substituted $C_1$ to $C_3$ alkoxy, $NH_2$, $C_1$ to $C_3$aminoalkyl, substituted $C_1$ to $C_3$ aminoalkyl, $NO_2$, aryl, Substituted aryl, heterocyclic, or substituted heterocyclic. $R_2$ and $R_3$ are each independently selected from H, OH, halogen, $NH_2$, $N(R_B)_2$, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl aryl, substituted aryl, heterocyclic, substituted heterocyclic, or $COR_A$ wherein $R_A$ are $R_B$ are defined as above;

b) a compound having the general formula II

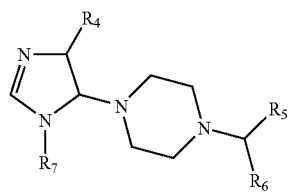

wherein $R_7$ is selected from H, OH, halogen, CN, $C_1$ to $C_6$ alkyl, substituted $C_1$ to $C_6$ alkoxy, substituted $C_1$ to $C_6$ alkoxy, $C_3$ to $C_6$ alkenyl, aryl, substituted aryl, heterocyclic, substituted heterocyclic, or $COR_A$ wherein $R_A$ is defined as above; $R_4$, $R_5$ and $R_6$ are each independently selected from H, OH, halogen, $NH_2$, $N(R_B)_2$, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, $COR_A$ wherein $R_A$ and $R_B$ are defined as above, aryl substituted aryl, heterocyclic, or substituted heterocyclic, and, in particular, a substituents benzene ring which may contain 1 or 2 heteroatoms selected from O, N and S, containing the substituents A, B, and C as shown below

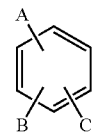

Wherein A, B, and C, are each independently selected from the group consisting of H, halogen, OH, CN, $C_1$ to $C_6$ alkyl, $C_1$ to $C_6$ substituted alkyl, $C_1$ to $C_6$ alkoxy, substituted $C_1$ to $C_6$ alkoxy $NH_2$, $C_1$ to $C_6$ aminoalkyl, substituted $C_1$ to $C_6$ aminoalkyl, $NO_2$, aryl, substituted aryl, heterocyclic or substituted heterocyclic;

c) a compound having the general formula III

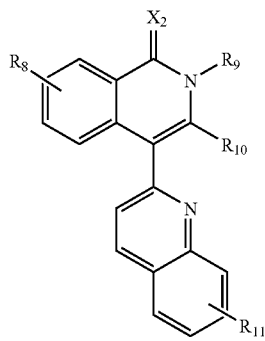

III wherein $X_2$ is selected from the group of O, or S;

$R_8$ is selected from H, OH, halogen, $NO_2$, $NH_2$, $N(R_B)_2$, CN, $C_1$ to $C_6$ alkyl, substituted $C_1$ to $C_6$ alkyl $C_1$ to $C_6$ alkoxy, substituted $C_1$ to $C_6$ alkoxy, $C_3$ to $C_6$ alkenyl, $COR_A$ wherein $R_A$ and RB are defined as above, aryl, Substituted aryl, heterocyclic, or substituted heterocyclic;

R9 is selected from H, OH, halogen, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, $COR_A$ wherein $R_A$ is defined as above, alkaryl group, aryl, substituted aryl, heterocyclic, or substituted heterocyclic and, in particular, a substituted benzene ring which may contain 1 or 2 heteroatoms selected from O, N and S, containing the substituents A, B, and C as shown below

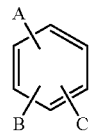

wherein A, B, and C are each independently selected from the group consisting of H, halogen, OH, CN, $C_1$ to $C_6$ alkyl, $C_1$ to $C_6$ substituted alkyl, $C_1$ to $C_6$ alkoxy, substituted $C_1$ to $C_6$ alkoxy, $C_1$ to $C_6$ $NH_2$, aminoalkyl, Substituted $C_1$ to $C_5$ aminoalkyl, $NO_2$, aryl, heterocyclic or substituted heterocyclic;

$R_{10}$ is selected from H, OH, halogen, $NH_2$, $N(R_B)_2$, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, COR A wherein $R_A$ and $R_B$ are defined as above, aryl, substituted aryl, heterocyclic, or substituted heterocyclic;

$R_{11}$ is selected from H, halogen, OH, CN, $NO_2$, $C_1$ to $C_6$ alkyl, $C_1$ to $C_6$ substituted alkyl, $C_1$ to $C_6$ alkoxy, substituted $C_1$ to $C_6$ alkoxy, $NH_2$, $N(R_B)_2$, e.g $C_1$ to $C_6$ aminoalkyl, substituted $C_1$ to $C_6$ aminoalkyl, $NO_2$, aryl, substituted aryl, heterocyclic, substituted heterocyclic, and $COR_A$ whereby $R_A$ and $R_B$ are defined as above;

d) a compound having the general formula IV

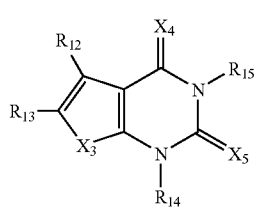

IV wherein X3 and X5 are independently selected from the group of O, and S, X4 is O, S or NRB, wherein RB is defined as above;

R12 is selected from of H, OH, CN, NO2 halogen, C1 to C6 alkyl, substituted C1 to C6 alkyl, C1 to C6 alkoxy, substituted C1 to C6 alkoxy NH2, C1 to C6 aminoalkyl, and substituted C1 to C6 aminoalkyl, aryl, substituted aryl, heterocyclic, or substituted heterocyclic;

R13 is selected from H, halogen, OH, CN, C1 to C6 alkyl, C1 to C6 substituted alkyl, C1 to C6 alkoxy, substituted c1 to C6 alkoxy, NH2, C1 to C6 aminoalkyl, substituted C1 to C6 aminoalkyl, NO2 aryl, substituted aryl, heterocyclic, or substituted heterocyclic; R14 and R15 are independently selected from H, OH, halogen, CN, C1 to C6 alkyl, substituted C1 to C6 alkyl, C1 to C6 alkoxy, substituted C1 to C6 alkoxy, C3 to C6 alkenyl, CORA wherein RA is defined as above, aryl, substituted aryl, heterocyclic, or substituted heterocyclic, preferably, a substituted benzene ring which may contain 1 or 2 heteroatoms selected from O, N and S, containing the substituents A, B and C as shown below,

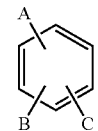

wherein A, B, and Care each independently selected from the group consisting of H, halogen, OH, CN, C1 to C6 alkyl, C1 to C6 substituted alkyl, C1 to C6 alkoxy, substituted C1 to C6 alkoxy, N(RB)2 e.g. C1 to C6 aminoalkyl, substituted C1 to C6 aminoalkyl, NO2, aryl, substituted aryl, heterocyclic, substituted heterocyclic, in particular, a six membered heterocyclic ring containing in its backbone 1 or 2 heteroatoms selected from the group consisting of O, S, and NRB wherein RA and RB are defined as above, and containing one or two independent substituents selected from the group consisting of H, halogen OH, CN, NO2, NH2, C1 to C3 alkyl, C1 to C3 alkoxy, and C1 to C3 aminoalkyl.

Preferably, the compound is a compound of the general formula IV or III, or pharmaceutically acceptable salts and solvates thereof, in particular, physiologically compatible acid and base addition salts.

In another aspect, the present invention relates to pharmaceutical compositions containing the compounds according to the present invention.

A further aspect of the present invention relates to methods of treating individuals having HPA, in particular, PKU comprising the step of administering to said individual a composition comprising as an active ingredient, a compound according to general formula I and/or a compound according to the general formula II and/or a compound according to the general formula III, and/or a compound according to the general formula IV as defined above or its pharmaceutically acceptable salts or solvates.

BRIEF DESCRIPTIONS OF THE DRAWINGS

FIG. 1. Four compounds found to stabilize PAH in the high throughput screening (HTS). A) Representative thermal denaturation profiles of wt-PAH in the absence (o) or presence of 100 μM of hit compounds 5 (Δ), 6 (◊), 11 (∇) and 13 (□), resulting from the HTS procedure as monitored by ANS fluorescence. B) Chemical structures of hit compounds 5 (5-amino-3-(5-methyl-3-phenyl-4-isoxazolyl)-1H-pyrazole-4-carbonitrile), 6 (1-benzhydryl-4-(1-methyl-4-nitro-1H-imidazol-5-yl)piperazine), 11 (3-amino-2-benzyl-7-nitro-4-(2-quinolyl)-1,2-dihydroisoquinolin-1-one) and 13 (5,6-dimethyl-3-(4-methyl-2-pyridinyl)-2-thioxo-2,3 dihydrothieno[2,3-d]pyrimidin-4(1H)-one).

Figure 2:
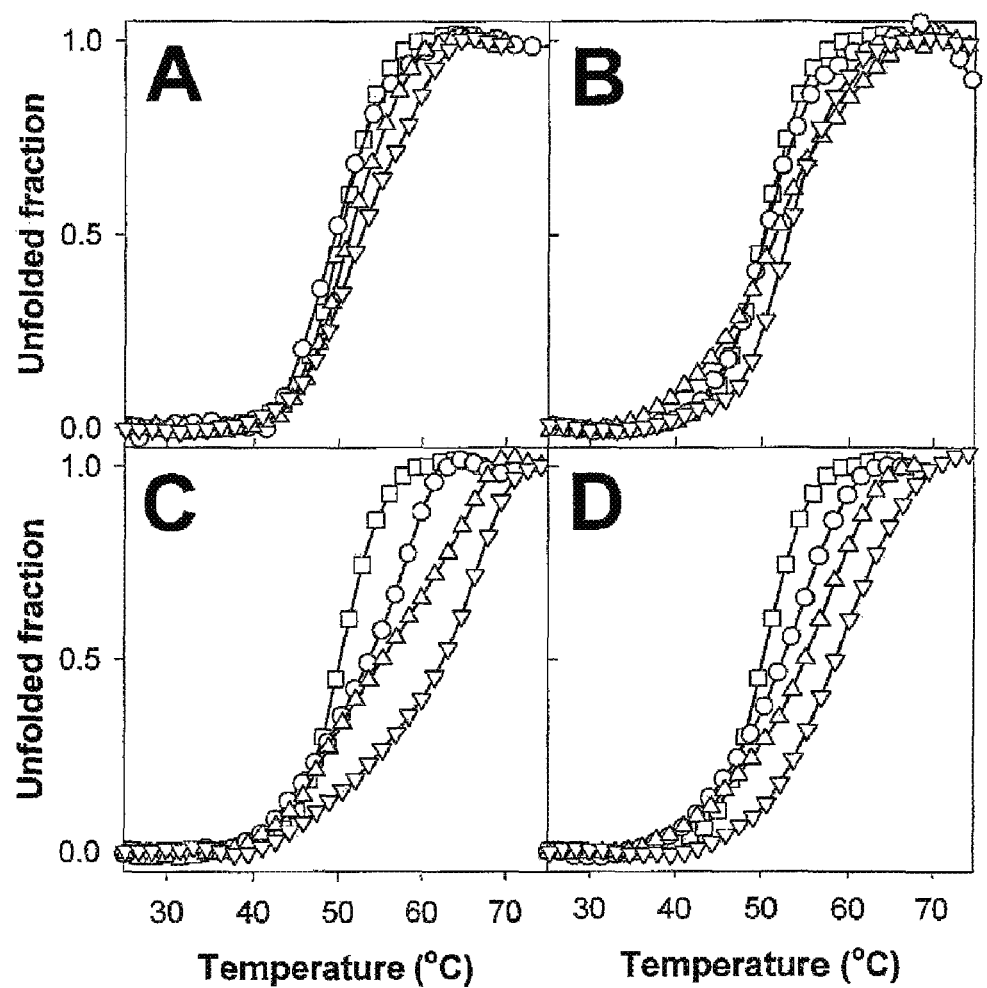

FIG. 2. FIG. 2 shows representative thermal denaturation profiles of wt-PAH in the absence or presence of different concentrations of hit compounds 5 (A), 6 (B), 11 (C) and 13 (D). Experiments were performed using 0 (□), 25 (○), 50 (Δ), 100 (∇) μM of the hit compounds. Plots are representative of at least three independent experiments.

Figure 3:
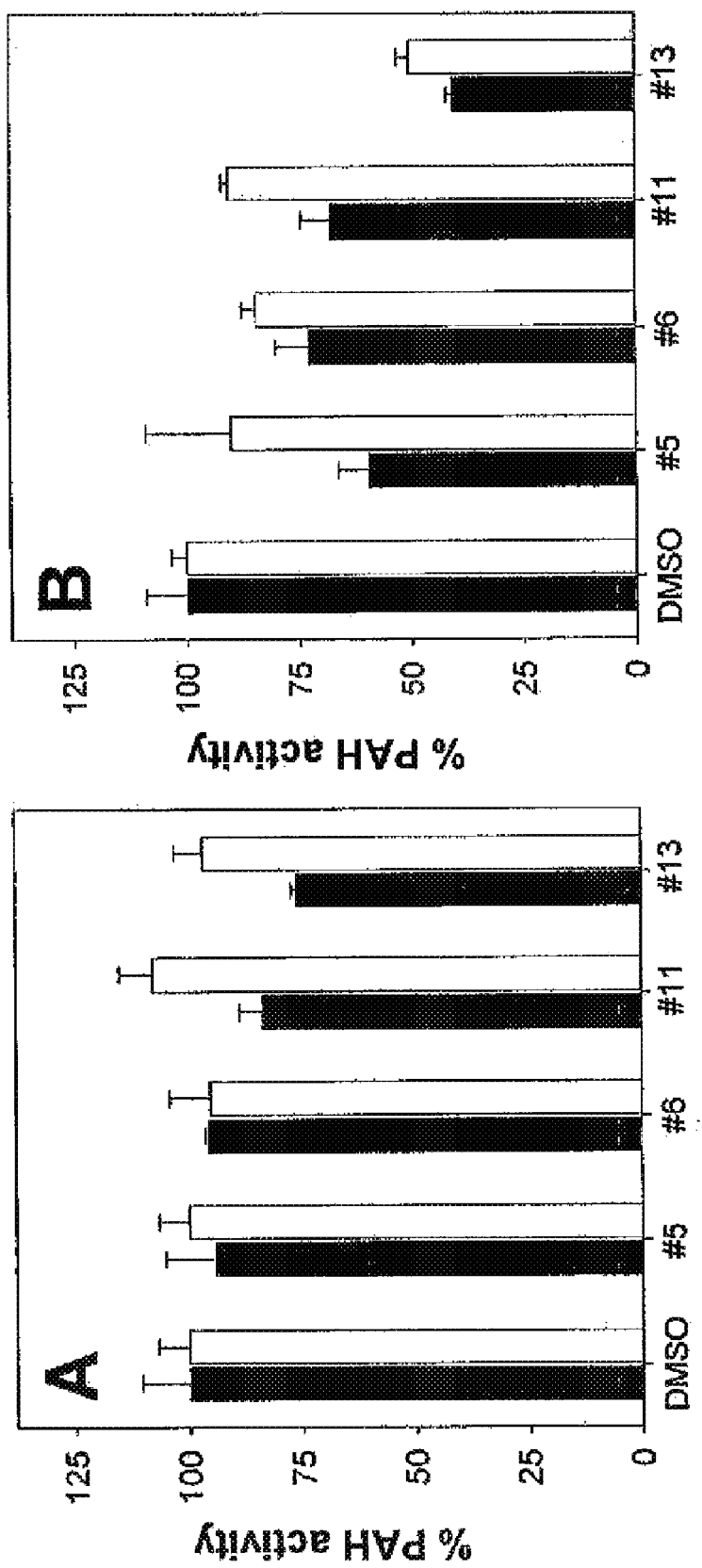

FIG. 3. FIG. 3 shows the effect of the hit compounds on the activity of recombinant PAH at standard conditions, in order to investigate putative inhibition. Experiments were performed at 100 μM of each compound, with 100 μM L-Phe and 10 μM BH4 (A) or 1 mM L-Phe and 200 μM BH4 (B). Samples were preincubated (black) or no preincubated (white) with L-Phe prior to activity measurement. Data are mean±SD of triplicate experiments.

Figure 4:
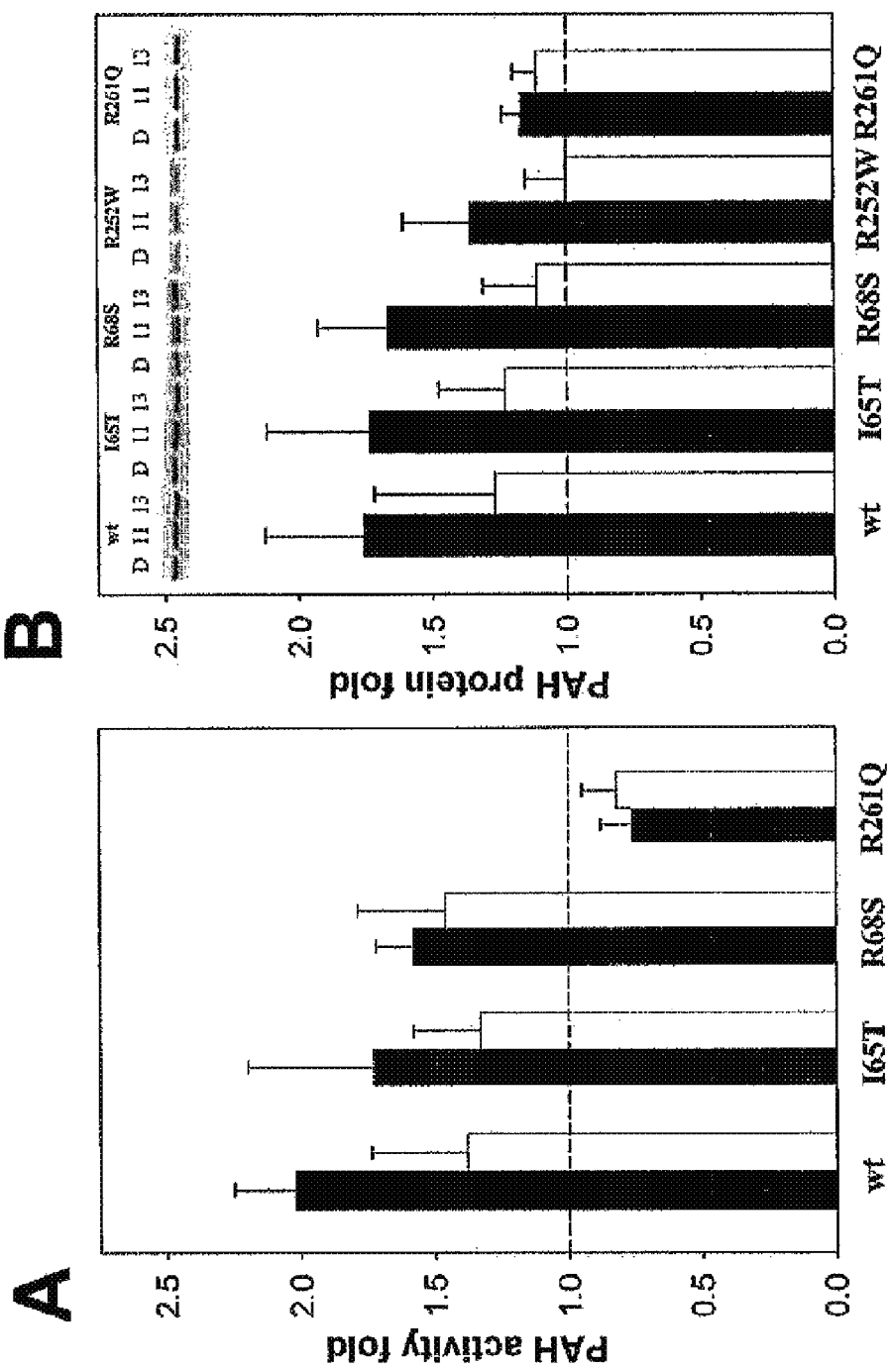

FIG. 4. FIG. 4 provides the effect of the hit compounds 11 (black) and 13 (white) on wt-PAH and PKU mutants transiently expressed in A293 cells. The concentration of the compounds was 40 μM. A) Effect on PAH activity levels. B) Effect on immunoreactive protein levels as measured by Western blot analysis. Activities and immunoreactive protein levels are expressed as ratio compared to controls in the presence of DMSO 1% for each PAH protein. Data are mean±SD of at least three expression experiments. Specific activities were: wt-PAH: 7.1±2.3; I65T-PAH: 1.7±0.6; R68S-PAH: 3.3±0.4; R261Q-PAH: 4.9±1.9 nmol L-Tyr/min·mg. Activities for R252W-PAH were lower than the detection limit of the assay (<0.01 nmol L-Tyr/min·mg protein) and thus, not considered reliable.

DETAILED DESCRIPTION OF THE PRESENT INVENTION

The present invention relates to the use of compounds having stabilizing activity on the PAH enzyme, thus, increasing the ratio of phenylalanine conversion to tyrosine in the body of an individual. Said compounds are useful for the preparation of medicaments for the prophylaxis and/or treatment of HPA, in particular of PKU, or diseases, disorders or conditions related thereto.

Namely, relatively low concentrations of the compounds according to the present invention which represents pharmacological chaperones for the phenylalanine hydroxylase (PAH) protein are able to significantly increase PAH residue activity and stability on the protein level of mutated PAH proteins.

In this connection, the term "pharmacological chaperones" refers to small molecules that stabilize protein native states, see e.g. Arawaka T, et al., Biochim Biophys Acta 2006; 1764 (11):1677-87, in contrast to chemical chaperones or osmolytes like glycerol or TMAO, which non-specifically stabilize compact native states mostly by preferential dehydration of the protein backbone and, therefore, increase the efficiency in correct folding (Arawaka T, et al, supra).

The term "therapy" or "treatment" refers to a process that is intended to produce a beneficial change in the condition of an individual like a mammal, e.g., a human, often referred to as a patient, or animal. A beneficial change can, for example, include one or more of: restoration function, reduction symptoms, limitation or retardation of progression of a disease, disorder, or condition or prevention, limitation or retardation of deterioration of a patient's condition, disease or disorder. Such therapy usually encompasses the administration of a drug, among others.

As used herein, the term "diseases, disorders and conditions" resulting thereform or relating thereto refers to diseases, disorders and conditions due to HPA and PKU, like mental retardation. In addition, disorders where PAH function is affected due to PAH inhibition or inactivation leading to HPA, like vitiligo, are included (Pey A L, et al. Faseb J 2006; 20(12):2130-2).

As used herein, the term "individual" or "subject" which is used herein interchangeably refers to an individual or a subject in need of a therapy or prophylaxis. Preferably, the subject or individual is a vertebrate, even more preferred a mammal, particularly preferred a human.

In one aspect, the present invention relates to the use of the compounds having the general formula I, a compound having the general formula II, a compound having the general formula III and/or a compound having the general formula IV and its physiologically compatible salts and solvates thereof for the prophylaxis and/or treatment of HPA, in particular, PKU, and diseases, disorders and conditions resulting therefrom.

A compound having the general formula I is shown below

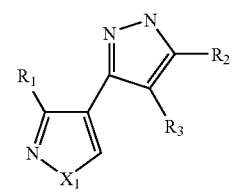

I wherein $X_1$ is O, S, $CR_A$ or $NR_B$;

$R_A$ is selected from the group of H, halogen, OH, CN, $C_1$ to $C_6$ alkyl, substituted $C_1$ to $C_6$ alkyl, $C_1$ to $C_6$ alkoxy, substituted $C_1$ to $C_6$ alkoxy, $NH_2$, $C_1$ to $C_6$ aminoalkyl, substituted $C_1$ to $C_6$ aminoalkyl, aryl, substituted aryl, heterocyclic, or substituted heterocyclic;

$R_B$ is selected from the group of H, $C_1$ to $C_6$ alkyl, substituted $C_1$ to $C_6$ alkyl, $C_1$ to $C_6$ alkoxy, substituted $C_1$ to $C_6$ alkoxy;

$R_1$ is selected from H, OH, halogen, $NH_2$, $N(R_B)_2$, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, aryl, substituted aryl, heterocyclic, substituted heterocyclic, $COR_A$ wherein $R_A$ and $R_B$ are defined as above, and, in particular, a substituted benzene ring which may contain 1 or 2 heteroatoms selected from O, N and S, containing the substituents A, B, and C as shown below

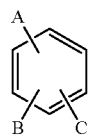

wherein A, B, and C are each independently selected from the group consisting of H, halogen, OH, CN, $C_1$ to $C_3$ alkyl, $C_1$ to $C_3$ substituted alkyl, $C_1$ to $C_3$ alkoxy, substituted $C_1$ to $C_3$ alkoxy, $NH_2$, $C_1$ to $C_3$ aminoalkyl, substituted $C_1$ to $C_3$ aminoalkyl, $NO_2$, aryl, substituted aryl, heterocyclic, or substituted heterocyclic;

$R_2$ and $R_3$ are each independently selected from H, OH, halogen, $NH_2$, $N(R_B)_2$, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, aryl, substituted aryl, heterocyclic, substituted heterocyclic, or $COR_A$ wherein $R_A$ and $R_B$ are defined as above;

In a particular preferred embodiment, general formula I is a compound wherein $X_1$ is O and $R_1$ is a substituted benzene ring containing the substituents A, B, and C as shown below

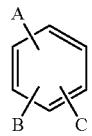

wherein A, B and C are each independently selected from the group consisting of H, halogen, OH, CN, $C_1$ to $C_3$ alkyl, $C_1$ to $C_3$ substituted alkyl, $C_1$ to $C_3$ alkoxy, substituted $C_1$ to $C_3$ alkoxy, $NH_2$, $C_1$ to $C_3$ aminoalkyl, substituted $C_1$ to $C_3$ aminoalkyl, $NO_2$, aryl, substituted aryl, heterocyclic, or substituted heterocyclic.

In another preferred embodiment, $R_3$ is a cyano group and/or $R_2$ is an amino group.

Particularly preferred, the compound of the general formula I is a compound wherein R1 is phenyl, R2 is an amino group, R3 is a cyano group and X1 is O.

In another preferred embodiment, the compound according to the present invention is a compound having the general formula II.

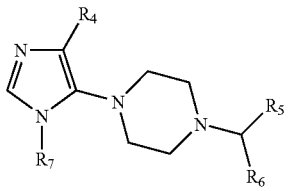

wherein $R_7$ is selected from H, OH, halogen, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, aryl, substituted aryl, heterocyclic, substituted heterocyclic, or $COR_A$ wherein $R_A$ is defined as above;

$R_4$, $R_5$ and $R_6$ are each independently selected from H, OH, halogen, NH2, N(RB)2, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, $COR_A$ wherein $R_A$ and $R_B$ are defined as above, aryl, substituted aryl, heterocyclic, or substituted heterocyclic, and, in particular, a substituted benzene ring which may contain 1 or 2 heteroatoms selected from O, N and S, containing the substituents A, B, and C as shown below

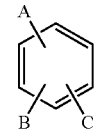

wherein A, B, and C are each independently selected from the group consisting of H, halogen, OH, CN, $C_1$ to $C_6$ alkyl, $C_1$ to $C_6$ substituted alkyl, $C_1$ to $C_6$ alkoxy, substituted $C_1$ to $C_6$ alkoxy, $NH_2$, $C_1$ to $C_6$ aminoalkyl, substituted $C_1$ to $C_6$ aminoalkyl, $NO_2$, aryl, substituted aryl, heterocyclic or substituted heterocyclic.

Preferably, the compound having the general formula II is a compound wherein $R_5$ and $R_6$ are a substituted benzene ring containing the substituents A, B, and C as shown below:

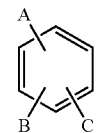

wherein A, B, and C are each independently selected from the group consisting of H, halogen, OH, CN, $C_1$ to $C_6$ alkyl, $C_1$ to $C_6$ substituted alkyl, $C_1$ to $C_6$ alkoxy, substituted $C_1$ to $C_6$ alkoxy, $NH_2$, $C_1$ to $C_6$ aminoalkyl, substituted $C_1$ to $C_6$ aminoalkyl, $NO_2$, aryl, or substituted aryl;

In another embodiment, $R_7$ is a $C_1$-$C_4$ alkyl group which may be substituted. Furthermore, $R_4$ is preferably a nitro group or a halogen.

Particular preferred, the compound of the general formula II is a compound wherein $R_7$ is methyl, $R_4$ is nitro and $R_5$ and $R_6$ are phenyl which may be substituted.

Another preferred embodiment relates to the use of compounds having the general formula III

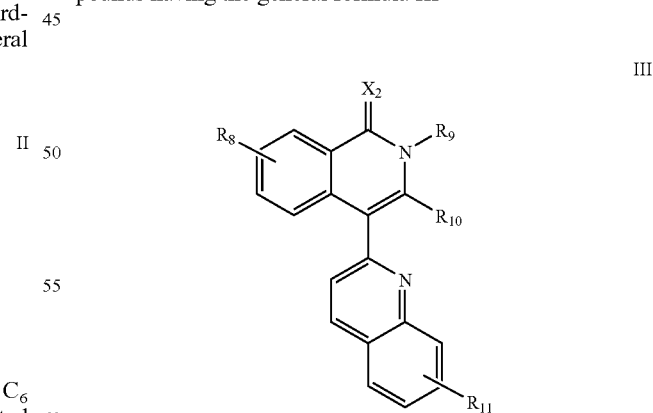

wherein $X_2$ is selected from the group of O, or S;

$R_8$ is selected from H, OH, halogen, $NO_2$, $NH_2$, $N(R_B)_2$, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, $COR_A$ wherein $R_A$ and $R_B$ are defined as above, aryl, substituted aryl, heterocyclic, or substituted heterocyclic;

$R_9$ is selected from H, OH, halogen, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, $COR_A$ wherein $R_A$ is defined as above, alkaryl group, aryl, substituted aryl, heterocyclic, or substituted heterocyclic and, in particular, a substituted benzene ring which may contain 1 or 2 heteroatoms selected from O, N and S, containing the substituents A, B, and C as shown below

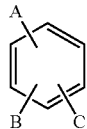

wherein A, B, and C are each independently selected from the group consisting of H, halogen, OH, CN, $C_1$ to $C_6$ alkyl, $C_1$ to $C_6$ substituted alkyl, $C_1$ to $C_6$ alkoxy, substituted $C_1$ to $C_6$ alkoxy, $C_1$ to $C_6$ $NH_2$, aminoalkyl, substituted $C_1$ to $C_6$ aminoalkyl, $NO_2$, aryl, substituted aryl, heterocyclic or substituted heterocyclic;

$R_{10}$ is selected from H, OH, halogen, $NH_2$, $N(R_B)_2$, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, $COR_A$, wherein $R_A$ and $R_B$ are defined as above, aryl, substituted aryl, heterocyclic, or substituted heterocyclic;

$R_{11}$ is selected from H, halogen, OH, CN, $NO_2$, $C_1$ to $C_6$ alkyl, $C_1$ to $C_6$ substituted alkyl, $C_1$ to $C_6$ alkoxy, substituted $C_1$ to $C_6$ alkoxy, $NH_2$, $N(R_B)_2$, e.g. $C_1$ to $C_6$ aminoalkyl, substituted $C_1$ to $C_6$ aminoalkyl, $NO_2$, aryl, substituted aryl, heterocyclic, substituted heterocyclic; and $COR_A$ whereby $R_A$ and $R_B$ are defined as above.

Particular preferred are compounds of the general formula III wherein $X_2$ is O and $R_9$ is a substituted benzene ring containing the substituents A, B, and C as shown below

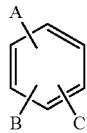

wherein A, B, and C are each independently selected from the group consisting of H, halogen, OH, CN, $C_1$ to $C_3$ alkyl, $C_1$ to $C_3$ substituted alkyl, $C_1$ to $C_3$ alkoxy, substituted $C_1$ to $C_3$ alkoxy, $NH_2$, $C_1$ to $C_3$ aminoalkyl, substituted $C_1$ to $C_3$ aminoalkyl, $NO_2$, aryl, or substituted aryl.

Further preferred are compounds wherein $R_{10}$ is an amino group and/or $R_9$ is hydrogen and/or $R_8$ is $NO_2$.

Particular preferred, is a compound of the general formula III wherein $R_8$ is a nitro group, $R_9$ is a benzyl group, $R_{10}$ is an amino group and $R_{11}$ is hydrogen.

Furthermore, another embodiment relates to the use of compounds having the general formula IV

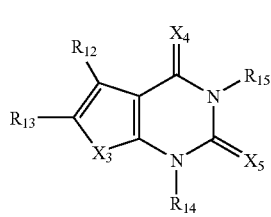

IV wherein $X_3$ and $X_5$ are independently selected from the group of O, and S, $X_4$ is O, S or $NR_B$; wherein $R_B$ is defined as above;

$R_{12}$ is selected from of H, OH, CN, $NO_2$, halogen, $C_1$ to $C_6$ alkyl, substituted $C_1$ to $C_6$ alkyl, $C_1$ to $C_6$ alkoxy, substituted $C_1$ to $C_6$ alkoxy, $NH_2$, $C_1$ to $C_6$ aminoalkyl, and substituted $C_1$ to $C_6$ aminoalkyl, aryl, substituted aryl, heterocyclic, or substituted heterocyclic;

$R_{13}$ is selected from H, halogen, OH, CN, $C_1$ to $C_6$ alkyl, $C_1$ to $C_6$ substituted alkyl, $C_1$ to $C_6$ alkoxy, substituted $C_1$ to $C_6$ alkoxy, $NH_2$, $C_1$ to $C_6$ aminoalkyl, substituted $C_1$ to $C_6$ aminoalkyl, $NO_2$, aryl, substituted aryl, heterocyclic, or substituted heterocyclic;

$R_{14}$ and $R_{15}$ are independently selected from H, OH, halogen, CN, $C_1$ to $C_6$ alkyl, substituted $C_1$ to $C_6$ alkyl, $C_1$ to $C_6$ alkoxy, substituted $C_1$ to $C_6$ alkoxy, $C_3$ to $C_6$ alkenyl, $COR_A$ wherein $R_A$ is defined as above, aryl, substituted aryl, heterocyclic, or substituted heterocyclic, preferably, a substituted benzene ring which may contain 1 or 2 heteroatoms selected from O, N and S, containing the substituents A, B, and C as shown below,

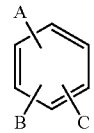

wherein A, B, and C are each independently selected from the group consisting of H, halogen, OH, CN, $C_1$ to $C_6$ alkyl, $C_1$ to $C_6$ substituted alkyl, $C_1$ to $C_6$ alkoxy, substituted $C_1$ to $C_6$ alkoxy, $N(R_B)_2$, e.g. $C_1$ to $C_6$ aminoalkyl, substituted $C_1$ to $C_6$ aminoalkyl, $NO_2$, aryl, substituted aryl, heterocyclic, substituted heterocyclic, in particular, a six membered heterocyclic ring containing in its backbone 1 or 2 heteroatoms selected from the group consisting of O, S, and $NR_B$ wherein $R_A$ and $R_B$ are defined as above, and containing one or two independent substituents selected from the group consisting of H, halogen, OH, CN, $NO_2$, $NH_2$, $C_1$ to $C_3$ alkoxy, and $C_1$ to $C_3$ aminoalkyl.

In particular, the compound is a compound of the general formula IV wherein $X_3$ and $X_5$ are S, $X_4$ is O and $R_{14}$ is a six membered heterocyclic ring containing in its backbone 1 or 2 heteroatoms selected from the group consisting of O, S, $NR_B$ wherein $R_B$ is defined as above, and containing one or two independent substituents selected from the group consisting of H, halogen, OH, CN, $NO_2$, $NH_2$, $C_1$ to $C_3$ alkyl, $C_1$ to $C_3$ alkoxy, and $C_1$ to $C_3$ aminoalkyl.

In a further preferred embodiment, a compound of the general formula IV is used wherein $R_{12}$ and $R_{13}$ are methyl, $X_3$ is S, $R_{14}$ is methylpyridinyl, $X_4$ is O, $X_5$ is S and $R_{15}$ is hydrogen.

The term "alkyl" is used herein to refer to both straight- and branched-chain saturated aliphatic hydrocarbon groups having 1 to 6 carbon atoms unless otherwise indicated; "alkenyl" is intended to include both straight- and branched-chain alkyl group with 1 or 2 carbon-carbon double bonds and containing 2 to 8 carbon atoms unless otherwise indicated.

The terms "substituted alkyl", and "substituted alkenyl" refer to alkyl, and alkenyl as just described having one or more substituents from the group including halogen, CN, OH, $NO_2$, amino, carbonyl, keto, aryl, heterocyclic, substituted aryl, substituted aryl, substituted heterocyclic, alkoxy, aryloxy, substituted alkyloxy, alkylcarbonyl, alkylcarboxy, alkylamino, arylthio. These substituents may be attached to any carbon of the alkyl, or alkenyl group provided that the attachment constitutes a stable chemical moiety.

The term "aryl" is used herein to refers to an aromatic system which may be a single ring or multiple aromatic rings fused or linked together as such that at least one part or the fused or linked rings forms the conjugated aromatic system. The aryl groups include, but are not limited to, phenyl, naphthyl, biphenyl, anthryl, tetrahydronaphthyl, phenanthryl.

The term "heterocyclic" is used herein to describe a stable 4- to 11-membered monocyclic or a stable multicyclic heterocyclic ring which is saturated, partially unsaturated, or unsaturated, and which consists of carbon atoms and from one to four heteroatoms selected from the group including N, O, an S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, but are not limited to, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having 1 to 4 substituents selected from the group which includes halogen, CN, OH $NO_2$, amino, alkyl, substituted alkyl, cyclically, alkenyl, alkoxy, aryloxy, substituted alkyloxy, alkylcarbonyl.

The term "alkoxy" is used herein to refer to the OR group, where R is alkyl or substituted alkyl, containing 1 to 6 carbon atoms.

The term "aminoalkyl" refers to both secondary and tertiary amines wherein the alkyl or substituted alkyl groups, containing 1 to 6 carbon atoms, which may be either the same or different and the point of attachment is on the nitrogen atom. The term "halogen" refers to Cl, Br, R or I.

In a further aspect, the present invention relates to a pharmaceutical composition comprising a compound of the general structure I and/or a compound of the general formula IV or its physiologically acceptable salts or solvates as defined herein optionally together with an pharmaceutically acceptable carrier.

As used herein, the term "carrier" refers to a diluent, adjuvant, excipient, or vehicle.

Thus, in a further aspect, the present invention relates to pharmaceutical compositions comprising compounds according to formula (I), (II), (III) or (IV) or salts or solvates thereof and, optionally a pharmaceutically acceptable carrier. Such pharmaceutical compositions comprise a therapeutically effective amount of the compounds and, optionally, a pharmaceutically acceptable carrier. The pharmaceutical compositions may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts or wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin ($18^{th}$ ed., Mack Publishing Co., Easton, Pa. (1990)). Such compositions will contain a therapeutically effective amount of the aforementioned compounds containing compounds according to formula (I) and (II), salts or solvates thereof, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilising agent and a local anesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes or a disease, or any other desired alteration of a biological system. In the present invention, the result will typically involve an increase in the immunological responses to infection or a suppression of the responses to inflammatory processes.

In vitro assays may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model text systems. Preferably, the pharmaceutical composition is administered directly or in combination with an adjuvant.

The term "administered" means administration of a therapeutically effective dose of the aforementioned pharmaceutical composition comprising the compounds containing the compound according to formula (I), (II), (III) and (IV) salts and solvates thereof as defined herein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age body weight, general health, sex, diet, time of administration drug interaction and the severity of the condition may be necessary, and will be ascertainable with routine experimentation by those skilled in the art.

In still another embodiment, the present invention relates to methods of prophylaxis and treating individuals suffering from hyperphenylalaninemia (HPA), in particular, phenylketonuria (PKU) and diseases, disorders and conditions related thereto comprising the step of administering to said individual an effective amount of a pharmaceutical comprising a compound according to formula (I), (II), (III) or (IV) or salts or solvates thereof as the active ingredient, and, optionally, a pharmaceutically acceptable carrier, in particular, the method is useful for preventing or treating HPA and PKU.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of was as discussed above, including, but not limited to, orally, subcutaneously, intravenously, intraarterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 mg, like 0.001 to 1000 pg; however, doses below or above this exemplary range are envisioned, especially considering the aforementioned factors.

Preferably, the pharmaceutical composition according to the present invention is a controlled-release pharmaceutical preparation, e.g. present in the form of capsules, tablets, pills, matrix or gels.

A controlled-release pharmaceutical preparation, according to the present invention, is one that achieves release of the compounds according to the present invention over an extended period of time, thereby extending the duration of therapeutic action and/or availability over that achieved by conventional delivery. An extended period of time may be from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44. 45, 46, 47, 48 hours or more and is in contrast to immediate release formulations that typically provide most, if not all, of a therapeutic agent in minutes after being administered to a subject. There may be a variability in time release and other characteristics associated with the administration of the compositions of the invention from subject to subject, so that time release profiles, dosage amounts, and other physical characteristics may be approximations. "Controlled-release pharmaceutical preparation", as used herein, is meant to include sustained-release formulations as well as time-release formulations.

In certain embodiments, the composition may be provided in various preparations or formulations, such as a capsule, tablet, pill, matrix, depot, or gel. The amount of the compounds according to the present invention may be provided in the approximate amounts of 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, or 100 mg or more, including any intervening values or ranges therein. the compounds according to the present invention may be released over approximate duration of at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or more hours. The composition may be administered by oral, injectable, depot or other route.

In some embodiments, a composition may include a number of regions, meaning 2, 3, 4, 5, 6, 7, 8, 9, 10, 15, 20, 25, 30 or more regions, that release the compounds according to the present invention ant differing rates. Such compositions may have one region that releases said compounds or one type of compounds at a higher rate, such as an immediate release region that releases a majority of therapeutic agent contained in that region upon exposure to gastrointestinal, vascular, or other body environments, as compared to a second region. Furthermore, a second region may be a controlled-released region that releases the same compound or a different compound for an appropriate time period, as described above. The present invention includes methods of treating a patient with HPA by administering the compositions described herein. In certain embodiments, a patient may be administered a dosage of the compounds according to the present invention in an approximate range 0.1, 0.2, 0.3, 0.4, 0.5, 0.6, 0.7, 0.8, 0.9, 1, 2, 3, 4, 5, 6, 7, 8, 9 mg/kg of body weight to 10, 11, 12, 13, 14, 15, 16, 17, 18, 19, 20 mg/kg of body weight.

In certain embodiments of the present invention, a sustained-, time-, or otherwise controlled-release formulation of the compounds according to the present invention can be used alone or in combination with other active ingredients for treatment of HPA and, in particular, PKU the compounds according to the present invention alone or in combination with other active ingredients may be administered as a single formulation or multiple formulations with controlled, sustained, or time release kinetics that may be determined and produced by one skilled in the production of such therapeutic vehicles (for example, as described in Remington's Pharmaceutical Sciences 16$^{th}$ Edition, Mack Publishing Company 1980, Ed. A. Osol and Tailored Polymeric Materials for Controlled Delivery Systems, ACS Symposium Series, No. 709, Eds. McCulloch and Shalaby, which are hereby incorporated by references).

In other embodiments of the invention, a sustained-, time-, or otherwise controlled-release formulation may include multiple regions or "compartments" in a delivery vehicle, which will allow release of a therapeutic agent(s) at different rates, such as an immediate release region combined with a controlled, sustained or time release region. The differing release rates may be incorporated into a single drug delivery vehicle or multiple drug delivery vehicles. The drug delivery vehicles may contain the compounds according to the present invention and other ingredients, such as protective compounds (e.g., antioxidants). Methods for the treatment of HPA and PKU using the sustained-, time-, or otherwise controlled-release drug delivery vehicles or formulations are contemplated.

Thus, in a further embodiment, the present invention relates to a method of treating an individual with HPA, in particular, PKU, said method comprising: administering, to the individual, a composition comprising as an active ingredient, a compound according to general formula I, and/or compound according to the general formula II, and/or a compound according to the general formula III, and/or a compound according to the general formula IV or its physiologically acceptable acid addition salts or solvates as defined herein.

Preferably, the composition provided is a pharmaceutical composition according to the present invention.

The present invention may be further understood by the following non-limiting examples.

EXAMPLES

Materials

The mutations 165T (SEQ ID NO: 2), R68S (SEQ ID NO: 3), R252W (SEQ ID NO: 4) and R261Q (SEQ ID NO: 5) were introduced in the human PAH cDNA (SEQ ID NO: 1) on the pcDNA3-PAH expression vector Knappskog P M, et al., Hum. Mutat. 1996; 8:236-246 by polymerase chain reaction (PCR)-based site-directed mutagenesis using the QuikChange™ kit (Stratagene). The primers used for mutagenesis (165T-PAH mutant sense (forward) primer (SEQ ID NO: 6); 165T-PAH mutant anti-sense (reverse) primer (SEQ ID NO: 7); R68S-PAH mutant sense (forward) primer (SEQ ID NO: 8); R68S-PAH mutant anti-sense (reverse) primer (SEQ ID NO: 9); R252W-PAH mutant sense (forward) primer (SEQ ID NO: 10); R252W-PAH mutant anti-sense (reverse) primer (SEQ ID NO: 11); R261Q-PAH mutant sense (forward) primer (SEQ ID NO: 12); and R261Q-PAH mutant anti-sense (reverse) primer (SEQ ID NO: 13)) were provided by MWG Biotech AG (Ebersberg). The authenticity of the mutagenesis was verified by DNA sequencing.

Recombinant Expression of PAH in E. coli

The tetrameric full-length wild-type (wt)-PAH (SEQ ID NO: 1), the R68S-PAH mutant (SEQ ID NO: 3) and the double truncated form $PAH_{103-428}$ (comprising residues 103-428 corresponding to the catalytic domain of the enzyme) (SEQ ID NO: 14) were recombinantly expressed in E. coli as fusion proteins with maltose binding protein (MBP), and further cleaved and isolated without the MBP fusion partner to homogeneity essentially as described Martinez A, et al., Biochem. J. 1995; 306:589-597.

High-Throughput Screening (HTS)

HTS for ligand-induced PAH stabilization was performed by monitoring the thermal denaturation of recombinant pure PAH protein in the presence of the extrinsic fluorescent probe 8-anilino 1-naphtalene sulfonic acid (ANS; Aldrich). HTS experiments were performed in a FluoDia T70 High Temperature Fluorescence Microplate Reader (Photon Technology International). Protein-ligand solutions (200 uL) were dispensed into 96-well microplates (ThermoFast®96 Skirted from Abgene) and overlayed with mineral oil. Protein solutions contained 0.1 mg/ml PAH (2 μM in PAH subunit) in 20 mM Hepes 200 mM NaCl pH 7.0 and 100 μM ANS. Ligands were added in DMSO, at 100 μM and 2.5% final concentration, respectively. Control experiments in the absence of DMSO and/or ligands were routinely performed in each microplate. Ligands (from MayBridge HitFinder™ Collection Database) were manually added to the microplates containing the protein solutions and incubated at 25° C. for 30 min before loading them onto the microplate reader. Thermal denaturation was monitored by following the increase in ANS fluorescence intensity due to protein unfolding $\lambda_{exc}$=395 and $\lambda_{em}$=500 nm; filters (Matulis D, et. Al., Biochemistry 2005, 44(13):5258-66). Fluorescence was registered in the 25-75° C. range, at a 1° C./min scan rate and allowing the system to equilibrate at each temperature for 1 min before fluorescence acquisition The experiments were real-time monitored using the software provided by the manufacturer. After smoothing and normalization of the experimental data, ligand induced stabilization was screened by estimation of the $T_{0.5}$ as mid-point temperature of the transition defined as the temperature where half of the unfolded fluorescence signal (fu) is experimentally observed, using a home-built software written in C++ and the following expression (equation 1):

$$fu = \frac{(F - (mn \cdot T + Yn)}{(mu \cdot T + Yu) - (mn \cdot T + Yn)}$$

Where F is the experimental fluorescence, mn and mu are pre and post-transition slopes and Yn and Yu are the intercepts, n and u are the native and unfolded states in the denaturation curves, which were normalized using pre and post transition linear baselines on temperature (T). Positives were confirmed by manual fitting of each positive hit to equation 1 in order to discard false positives generated during the automatic analysis procedure. Positive hits for stabilizing ligands were considered as those compounds that increased thermal stability beyond 2 times S.D.) ($T_{0.5(hit)}$>$T_{0.5(control)}$+(2 s.d.)), being $T_{0.5(control)}$ experimentally determined for each experiment (microplate) using controls in the absence of ligand and S.D. was the standard deviation of control experiments in each run (4-8 experiments in each microplate).

Thermal Denaturation Monitored by Fluorescence

Additional thermal denaturation experiments were performed on a Cary Eclipse fluorescence spectrophotometer equipped with a temperature controlled Peltier multicell holder (Varian). Samples containing PAH (2 μM subunit) in 20 mM NaHepes, 200 mM NaCl, pH 7.0, 100 μM ANS, 2.5% DMSO and 0-100 μM ligands were incubated at room temperature for 30 min to allow equilibration prior to measurements. Thermal denaturation was monitored by following changes in ANS fluorescence emission (excitation at 395 and emission at 500 nm; slits 10 nm) at a 1 K/min in a 20-80° C. range. Each run contained 4 different samples, including a control in the absence of ligand. Data analysis was performed by fitting of the experimental fluorescence to equation 1.

HTS searching for PAH stabilizing ligands (pharmacological chaperones) was performed by monitoring the effects of ligand binding on the thermal stability of wt-PAH by measuring the increase in ANS fluorescence upon protein denaturation, Matulis D, et. al., supra. ANS and DMSO concentrations were optimized to have little or no impact on PAH thermal stability and to display good signal-to-noise ratios. Under optimal conditions, the thermal denaturation of wt-PAH showed a mid-point transition temperature at about 47° C. This thermal transition is probably the result of two overlapping unfolding unfolding transitions, corresponding to regulatory ($T_m$=45° C.) and catalytic ($T_m$=54° C.) domain unfolding by circular dichroism spectroscopy and differential scanning calorimetry (DSC) (Thórólfsson M, et. Al., Biochemistry 2002; 41(24):7573-7585), which are not clearly visualized at low protein concentrations used in the HTS method. Further validation of this method was performed by studying the stabilizing effect of the natural substrate (L-Phe) on PAH thermal stability in a concentration dependent manner (not shown), which provided results in agreement with previous studies on PAH thermal denaturation.

HTS was perfomed using 1000 chemical compounds randomly selected from a commercially available compound library (MayBridge HitFinder™ Collection Database). This chemical library comprises 16,000 lead compounds which are representative of ~87% of the ~400,000 pharmacophores in the world drug index (http://www.maybridge.com/). Comparison of $T_{0.5}$ Values obtained for experiments in the absence or presence of ligands allowed discriminating between those ligands that significantly stabilize PAH protein. This selection criterion revealed 14 compounds as potential hits compounds.

Further experiments were performed in a Standard cell fluorimeter under identical conditions as for the HTS, which allowed confirmation of a significant and reproducible stabilizing effect for four of those 14 compounds (FIG. 1). However, they showed different ability to stabilize wt-PAH (Table 1).

TABLE 1

Half denaturation temperatures ($T_{0.5}$) for wt-PAH, $PAH_{103-428}$ and R68S-PAH in the absence or presence of hit compounds (100 μM) measured by ANS-monitored thermal unfolding experiments.

| Compound | $PAH_{wt}$ | | $PAH_{103-428}$ | | $PAH_{R68S}$ | |
|---|---|---|---|---|---|---|
| | $T_{0.5}$ | $\Delta T_{0.5}$ | $T_{0.5}$ | $\Delta T_{0.5}$ | $T_{0.5}$ | $\Delta T_{0.5}$ |
| No ligand | 49.5 ± 1.2 | — | 44.9 ± 0.4 | — | 48.9 ± 0.5 | — |
| #5 | 52.1 ± 0.9 | 2.6 | 49.2 ± 1.2 | 4.3 | 50.0 ± 1.4 | 1.1 |
| #6 | 52.2 ± 1.3 | 2.7 | 53.3 ± 1.5 | 8.4 | 52.1 ± 1.6 | 3.2 |
| #11 | 63.1 ± 2.9 | 13.6 | 55.0 ± 1.3 | 10.1 | 57.1 ± 0.3 | 8.2 |
| #13 | 56.7 ± 1.5 | 7.2 | 46.1 ± 0.7 | 1.2 | 50.5 ± 0.5 | 1.6 |

Data are mean ± SD from at least three independent experiments.
$T_{0.5}$ and $\Delta T_{0.5}$ are expressed in ° C.

As expected, the stabilizing effect was concentration dependent for all four of them, being significant at 25 μM for compounds 11 and 13 (FIG. 2). It is worth saying that the magnitude of the protein stabilization by ligands is dependent, among other factors, on the binding affinity and ligand concentration suggesting the following affinity ranking for those 4 compounds: 11>13>5≈6. The apparent affinities of wt-PAH for these four ligands were further studied by monitoring quenching effects of these ligands on PAH Trp-emission fluorescence (not shown). Ligands 11 and 13 induced significant fluorescence quenching, inducing a 50% decrease in Trp-fluorescence at ~30 and ~3 μM for ligands 11 and 13, respectively.

Similar ligand-induced stabilization experiments were performed using i) a double truncated form of PAH equivalent to the catalytic domain ($PAH_{103-428}$) lacking both the regulatory N-terminal domain and the tetramerization motif and existing as a functional dimmer and ii) the R68S-PAH mutant, associated to mild PKU and one of the few PKU mutants that display enough stability to be purified as a stable tetramer. At 100 μM concentration of ligand, hit compounds 6 and 11 significantly stabilized both $PAH_{103-428}$ and R68S-PAH (Table 1). Interestingly, these enzyme forms were only a slight stabilized by compound 13, suggesting that the regulatory domain plays an important role on its binding to PAH.

Enzyme Kinetic Analysis

PAH activity was measured at 25° C. for 1 min essentially as described (BjØrgo E, et al., Eur. J. Biochem. 1988; 257(1): 1-10). Tetrameric hPAH (1-2 μg) was incubated in 20 mM Hepes 0.2 M NaCl pH 7.0, containing catalase (0.04 mg/ml), 0.1-1 mM L-Phe, DMSO 2.5% and 0-100 μM of each compound. After 4 min incubation at 25° C., ferrous ammonium sulphate (100 μM) was added, and the reaction was triggered after 1 min by adding $BH_4$ (10-200 μM) in the presence of 5 mM DTT. In some experiments, the preincubation step with L-Phe was omitted and L-Phe was added together with $BH_4$ to analyze the L-Phe induced activation of the enzyme. To determine the kinetic parameters for $BH_4$ and L-Phe, $BH_4$ was used at 0-200 μM (at fixed 1 mM L-Phe) and L-Phe at 0-1 mM ($BH_4$ was fixed at 75 μM). L-Tyr formed was quantified by HPLC and fluorimetric detection (DØskeland A P, et al., J. Biol. Chem. 1984; 259:11242-11248). The saturation curves were fitted to hyperbolic (for $BH_4$) or sigmoidal (for L-Phe) kinetic models by using Sigma Plot v.9.0 (SPSS Inc).

PAH enzyme kinetics have been analyzed in the presence of the four hit compounds in order to know if ligand binding interferes with PAH catalytic activity. Activity measurements were performed in the presence of high (100 μM) concentrations of ligands with or without preincubating PAH enzyme with L-Phe prior to activity assays. L-Phe preincubation of human PAH lead to activation of the enzyme and manifestation of positive cooperativity by the substrate, and it is thought to play an important regulatory role on PAH activity in vivo (Pey A L, et al., In: Blau N. ed. Advances in PKU and BH4, 2006). By using low L-Phe and $BH_4$ concentrations (physiological concentrations; see references in Pey A L, et al., Mol Genet Metab 2005; 86 Suppl 1:S43-53.), moderate to weak inhibition was observed (FIG. 3A), specially significant for compounds 5 and 13. It is worth noting that under these conditions, ligand concentration equalled L-Phe concentration (100 μM), and 10-fold exceeded $BH_4$ concentration (10 μM). Except for compound 13, this inhibition was dramatically weakened when the preincubation step with L-Phe (100 μM) was ommited. Moreover, when L-Phe and $BH_4$ are used at saturating concentrations, inhibition was abolished (FIG. 3B), indicating a rather weak and reversible inhibitory effect exerted by these ligands.

Further kinetic analyses were performed to determine if the weak inhibition was due to competition for the substrate and/or cofactor binding sites. Activity dependence on $BH_4$ and L-Phe concentration was measured in the presence of 100 μM compound concentration, and the experimental data fitted to hyperbolic ($BH_4$) or sigmoidal (L-Phe) kinetic models. The fitting parameters obtained from these experiments are compiled in Table 2. Activity dependences on $BH_4$ concentrations (upon preincubation with saturating L-Phe concentrations, 1 mM), showed little or no effects of any of these ligands in the $V_{max}$ (lower than 15%), whereas compound 5 and 13 increased $K_m$ for $BH_4$ (~20% and 50%, respectively), suggesting a weak competitive behaviour vs $BH_4$ ($K_i$~500 μM and 200 μM, respectively using standard equations for competitive inhibition). These values are substantially higher than those obtained for likely physiological inhibitors of PAH, such as 7S-$BH_4$ and $BH_2$ ($K_i$~2-5 μM and ~17 μM, respectively). On the other hand, when the activity dependence on L-Phe concentration is analyzed (at high but not saturating $BH_4$ concentrations, 75 μM), no remarkable effects on $S_{0.5}$ or Hill coefficient (h) are observed, and only some reduction in $V_{max}$ is observed for Compounds 5 and 13 (about 13% and 30%), indicating a weak non-competitive inhibition, probably due to a primary competitive effect on $BH_4$ binding.

for 24 h in the presence or absence of 40 µM of hit compounds 11 and 13. Cell were harvested and immunoreactive PAH

TABLE 2

Enzyme kinetic parameters for wt-PAH in the presence of hit compounds (100 µM)

| Compound | $BH_4$[a] | | | | L-Phe[b] | | |
|---|---|---|---|---|---|---|---|
| | Preincubation | | No preincubation | | | | |
| | $V_{max}$ | $K_M$ | $V_{max}$ | $K_M$ | $V_{max}$ | $S_{0.5}$ | h |
| No ligand | 3.41 ± 0.24 | 41 ± 8 | 0.82 ± 0.03 | 23 ± 3 | 3.47 ± 0.07 | 116 ± 5 | 2.1 ± 0.2 |
| 5 | 3.52 ± 0.41 | 55 ± 14 | 0.80 ± 0.05 | 26 ± 5 | 3.02 ± 0.08 | 118 ± 5 | 2.6 ± 0.3 |
| 6 | 2.96 ± 0.10 | 36 ± 3 | 0.81 ± 0.05 | 24 ± 4 | 3.77 ± 0.13 | 156 ± 10 | 1.8 ± 0.1 |
| 11 | 2.87 ± 0.14 | 35 ± 4 | 0.86 ± 0.03 | 23 ± 3 | 3.57 ± 0.11 | 138 ± 8 | 1.9 ± 0.2 |
| 13 | 3.11 ± 0.16 | 66 ± 8 | 0.85 ± 0.07 | 36 ± 8 | 2.43 ± 0.10 | 131 ± 11 | 1.6 ± 0.2 |

Data are mean ± S.E. from non-linear regression analysis on two independent experiments performed in duplicate. $V_{max}$ in µmol L-Tyr/min·mg and $K_M$ and $S_{0.5}$ in µM.
[a]Parameters determined at 1 mM L-Phe and variable concentration of $BH_4$ (0-200 µM). Samples were preincubated or not (as indicated) with 1 mM L-Phe before activity measurements.
[b]Parameters determined at 75 µM $BH_4$ variable concentration of L-Phe (0-1 mM). Samples were preincubated at different L-Phe concentrations before activity measurements.

Expression Analysis of wt-PAH and Mutants in Eukaryotic Cells

Human embryonic kidney cells (A293; purchased from Invitrogen) were grown in Dulbecco's Modified Eagle's Medium (DMEM) containing 4.5 g/l glucose, 10% (v/v) fetal calf serum, 2 mM L-glutamine, 100 i.u./ml penicillin, 100 µg/ml streptomycin and 0.25 mg/ml G-418. A293 cells were transiently transfected with 1 µg of pcDNA3-PAH expression vector (wt or mutant PAH constructs), using the lipofectamine system (Gibco, Invitrogen) as described by the manufacturer. Pharmacological chaperones were added after 5 h of transfection (final concentration 40 µM ligand in DMSO 1%), incubated for 24 h and cells were then harvested and stored at −80° C. Control experiments in the absence of DMSO revealed no significant effects of 1% DMSO neither on PAH activity and immunoreactive protein nor cell growth and survival (data not shown).

Cell extracts were prepared by resuspending cell pellets in PBS buffer pH 7.4 containing 50 mM sucrose and the presence of 0.2 m M PMSF, 10 µg/ml of chymostatin, leupeptin, antipain and pepstatin. Cells were homogenized by 20 passages using a fine needle. Sucrose concentration was then raised to 0.25 M and extract were clarified by centrifugation at 170,000 g for 30 min at 4° C. Protein concentrations in cell extracts were normalized using Bradford assay and subsequently used for PAH inmunodetection and enzyme activity measurements.

Western blot analyses were performed after SDS-PAGE (10% acrylamide) using as primary antibody a monoclonal mouse ant-human PAH (Chemicon, Australia) and as secondary antibody a goat anti-mouse HRP conjugate (Bio-Rad, US). Detection was performed using a chemiluminiscence method (ECL; Amersham Biosciences) and quantified an a Fluor-S™ MultiImager (Bio-Rad, US) using Quantify one v. 4.5.2 software. Activity measurements were performed on cell extract after removal of free amino acids and contaminants of low molecular weight by using Zebra™ Desalt Spin columns (Pierce). 5-20 µg of total protein were used for activity measurements performed essentially as described above, using 1 mM L-Phe and 200 µM BH4 and 30 min reaction. Under these conditions, PAH immunoreactivity and activity were linear to the amount of PAH protein present in cell extracts.

After transfection of A293 cells with constructs carrying wt-PAH and PKU mutants cDNA, the cells were incubated protein and PAH activity were measured in soluble cell extracts. Result obtained are summarized in FIG. 4. The four PKU mutants tested, i.e. I65T- R68S-, R252W- and R261Q-PAH showed lower residual activity and steady-state protein levels compared to wt-PAH, reflecting folding defects to different extents, I65T-, R68S- andR261Q-PAH showed relatively high PAH activities compared to the wt controls (in the presence of DMSO 1%), i.e. 23%, 46% and 69% of wt activity, respectively. In the case of R252W-PAH, the activity was below the detection limit of the assay <0.2% of wt-PAH, both without and with Compounds 11 and 13), so analysis of the effects of the pharmacological chaperones on the enzyme activity were not considered. These result are consistent with previous expression analyses in eukaryotic systems (R68S=57±36%; I65T:41±33%; R261Q: 51±26%; R252W: 0%; and PAHdb at http://www.PAHDB.mcgill.ca/) within the experimental differences which may explain the experimental scatter observed between different reports, as previously pointed out (Waters P J. In: Blau N, ed. PKU and BH4. Advances in phenylketonuria and tetrahydrobiopterin. Heilbronn: SPS Verlagsgesellschaft MBH, 2006: 277.310). These four mutations may be considered as representatives of the different mutant folding behaviour associated to different phenotypic groups in PKU patients: R68S is a mild mutation, I65T is mild-moderate R261Q is highly variable (mild-moderate-severe) and R252W is a severe mutation.

Low concentrations (40 µM) of hit compounds 11 and 13 were able to enhance PAH expression in A293 cells to different extents, depending on the hit compound used and PAH protein expressed (FIG. 4). PAH activity was enhanced 60-100% by compound 11 and 40-50% by compound 13, in wt and I65T and R68S mutants (FIG. 4A). Enhancement of PAH activity correlated well with increase in PAH immunoreactive protein was observed in the presence of compound 11, while activity was too low to be accurately determined, probably due to a mixes effect of this mutation on both folding and catalytic efficiency of PAH protein. These effects were statistically significant in most of the cases for compound 11, but only in a few of them for compound 13 (FIG. 4).

These results clearly show that ligands which bind with significant affinity to PAH (as inferred from PAH stabilization observed by fluorescence spectroscopy) are able to increase protein levels and activity, probably protecting towards ubiquitin-mediated proteolytic degradation. Moreover, s similar correlation between ligand induced stabilization towards thermal denaturation (FIG. 2 and table 1) and enhancement of PAH activity and protein levels (FIG. 4) is found for both compounds and wt and mutant PAH proteins.

Experiments with Mice

This animal experiment was approved with permit 07-2008 for Professor Beat Thöny (available upon request), University of Zurich Children's Hospital.

Solutions of Compounds 11 and Compound 13 were prepared at concentrations of 5 mg/ml (14 mM) in 10% DMSO and 10% glucose. For that, stocks of 50 mg/ml (140 mM) of each compound in 100% DMSO were diluted 1:10 with a 10% glucose solution. Both the stocks and the final solutions of Compounds 11 and 13 are in fact suspensions since the compound is not soluble al these conditions.

Animal experiments were performed by Beat Töny (University of Zurich Children's Hospital). 25 µl/day of 10% DMSO (Group 1, control) or the solutions of Compound 11 (Group 2) or Compound 13 (Group 13) were administered orally for 10 days to young adult C57Bl/6 mice (all females) exactly 12 weeks old and with weight between 19 to 23 g were in each group, i.e. in Group 2 and 3 animals were given about 5.9 mg/kg/day. Five animals were treated in each group, and no weight change was experienced upon treatment, i.e. <5% change between start and end. Animals were sacrificed at day 10 of treatment, and their livers were sectioned in two frozen immediately in liquid nitrogen, then the frozen half-livers were sent to the Department of Biomedicine, University of Bergen in dry ice. Liver homogenates were prepared at 4° C. in presence of dithiothreitol (DTT) and the protease inhibitors phenylmethylsulfonyl fluoride, leupeptin, and pepstatin as described, Elzaouk L, et al. J Biol Chem 2003; 278(30): 28303-11. After homogeneization the extracts were clarified by centrifugation al 170,000 g for 30 min at 4° C.

The concentration of soluble protein was about 35 mg/ml of liver extract, similar in each group. The hepatic PAH response to oral supplementation of DMSO and of Compounds 11, 13 in 10% DMSO was analyzed b determining:

i) PAH activity, as described, after removal of free amino acids and contaminants of low molecular weight by using Zebra™ Desalt Spin columns(Pierce).

ii) Pah-mRNA expression by quantitative real-time PCR analysis, performed as reported A 1.65-fold increase in PAH activity was measured after treatment with Compound 11. An increase with Compound 13 was not significant (i.e. the measured activity was 1.27±0.63 for the Control group, 2.2±0.78 for Group 2 (Compound 11) and 1.41±0.54 for Group 3.

No change in Pah-mRNA expression by quantitative real-time PCR analysis in the treated mice compared to controls, supporting that Compound 11 does not affect gene expression or Pah-mRNA stability; the increased liver PAH activity would thus be a result of a stabilizing chemical-chaperon effect of Compound 11 on the enzyme.

Initial Conclusion from the Animal Experiments

These results constitute a proof of principle for the effect of Compound 11. The increase in activity is similar to that obtained by treatment of wild-type mice with tetrahydrobiopterin ($BH_4$), the natural cofactor of the enzyme, with 50 mg/kg by one intraperitoneal injection (1.6 increase in activity) or by oral treatment with 50 mg/kg/day during 5 weeks (1.7 increase in activity).

We are at present performing the Western blot analysis in these samples to measure the effect of the compounds on the PAH protein level. Moreover, we are planning a longer treatment for 5 weeks. For instance previous animal experiments have shown than although no effect was observed for 50 mg/kg/day oral treatment during 10 days, the effect was measurable after 5 weeks. Moreover, we expect that the absorption of the compounds is hampered by their insolubility providing a large variability in the concentration of compound accumulated in liver. Longer treatments may provide clearer results. Moreover, we presume that these compounds have to be improved for solubility to achieve a higher effect on PAH.

The invention claimed is:

1. A method of treating an individual with hyperphenylalaninemia (HPA), said method comprising:
administering to the individual a pharmacological chaperon having a stabilizing activity on phenylalanine hydroxylase (PAH) enzyme and its physiologically compatible addition salts and solvates, comprising, as an active ingredient,
a compound of formula IV

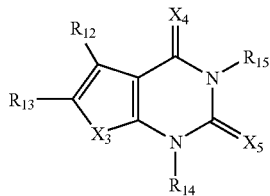

wherein:
$X_3$ and $X_5$ are independently selected from the group of O and S;
$X_4$ is O, S or $NR_B{'}$ wherein $R_B$ is selected from the group of H and $C_1$ to $C_6$ alkyl;
$R_{12}$ and $R_{13}$ are independently selected from H, $C_1$ to $C_6$ alkyl, aryl, substituted aryl, heterocyclic, or substituted heterocyclic; and
$R_{14}$ and $R_{15}$ are independently selected from H, $C_1$ to $C_6$ alkyl, $C_3$ to $C_6$ alkenyl, aryl, substituted aryl, heterocyclic, or substituted heterocyclic.

2. The method according to claim 1, wherein:
$X_3$ is O and $X_5$ is S;
$X_4$ is O;
$R_{12}$ $R_{13}$ and $R_{14}$ are independently selected from the group of H, $C_1$ to $C_6$ alkyl; and
$R_{15}$ is selected from the group of aryl, substituted aryl, heterocyclic and substituted heterocyclic.

3. The method according to claim 2, wherein $R_{15}$ is selected from the group of a 6-membered heterocylic ring containing in its backbone 1 or 2 heteroatoms selected from the group consisting of O, S and $NR_B$, wherein $R_B$ is as defined above, and containing one or two independent substituents selected from the group consisting of H and $C_1$ to $C_3$ alkyl.

4. The method according to claim 1 wherein the compound of formula IV is:

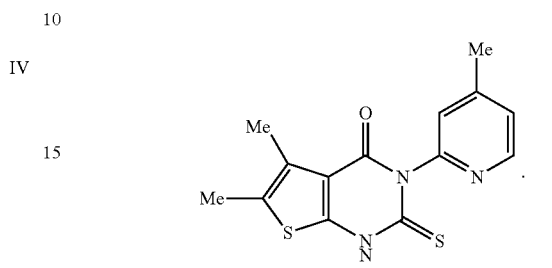

5. The method according to claim 1, for treating an individual with phenylketonuria (PKU).

6. A pharmaceutical composition comprising a compound of formula IV or its physiologically acceptable acid addition salts or solvates of claim 1.

7. The pharmaceutical composition according to claim 6 which is a controlled-release pharmaceutical preparation.

8. The pharmaceutical composition according to claim 6, wherein the composition is further defined as a capsules, tablet, pill, matrix or gel.

9. The pharmaceutical composition according to claim 6, wherein the active ingredient is released over a time period of greater than six hours during use.

10. The pharmaceutical composition according to claim 6 further defined as a depot formulation.

* * * * *

SEQUENCE LISTING

<160> NUMBER OF SEQ ID NOS: 14

<210> SEQ ID NO 1
<211> LENGTH: 1359
<212> TYPE: DNA
<213> ORGANISM: Homo sapiens

<400> SEQUENCE: 1

```
atgtccactg cggtcctgga aaacccaggc ttgggcagga aactctctga ctttggacag      60
gaaacaagct atattgaaga caactgcaat caaaatggtg ccatatcact gatcttctca     120
ctcaaagaag aagttggtgc attggccaaa gtattgcgct tatttgagga gaatgatgta     180
aacctgaccc acattgaatc tagaccttct cgtttaaaga aagatgagta tgaattttc      240 acccatttgg ataaacgtag cctgcctgct ctgacaaaca tcatcaagat cttgaggcat     300
gacattggtg ccactgtcca tgagctttca cgagataaga agaaagacac agtgccctgg     360
ttcccaagaa ccattcaaga gctggacaga tttgccaatc agattctcag ctatggagcg     420
gaactggatg ctgaccaccc tggttttaaa gatcctgtgt accgtgcaag acggaagcag     480
tttgctgaca ttgcctacaa ctaccgccat gggcagccca tccctcgagt ggaatacatg     540
gaggaagaaa agaaaacatg gggcacagtg ttcaagactc tgaagtcctt gtataaaacc     600
catgcttgct atgagtacaa tcacattttt ccacttcttg aaaagtactg tggcttccat     660
```

```
gaagataaca ttccccagct ggaagacgtt tctcaattcc tgcagacttg cactggtttc    720
cgcctccgac ctgtggctgg cctgctttcc tctcgggatt tcttgggtgg cctggccttc    780
cgagtcttcc actgcacaca gtacatcaga catggatcca agcccatgta taccccgaa     840 cctgacatct gccatgagct gttgggacat gtgcccttgt tttcagatcg cagctttgcc    900
cagttttccc aggaaattgg ccttgcctct ctgggtgcac ctgatgaata cattgaaaag    960
ctcgccacaa tttactggtt tactgtggag tttgggctct gcaaacaagg agactccata   1020
aaggcatatg gtgctgggct cctgtcatcc tttggtgaat acagtactg cttatcagag    1080 aagccaaagc ttctccccct ggagctggag aagacagcca tccaaaatta cactgtcacg   1140
gagttccagc ccctgtatta cgtggcagag agttttaatg atgccaagga gaaagtaagg   1200
aactttgctg ccacaatacc tcggcccttc tcagttcgct acgacccata cacccaaagg   1260
attgaggtct tggacaatac ccagcagctt aagattttgg ctgattccat taacagtgaa   1320
attggaatcc tttgcagtgc cctccagaaa ataaagtaa                           1359

<210> SEQ ID NO 2
<211> LENGTH: 452
<212> TYPE: PRT
<213> ORGANISM: Homo sapiens

<400> SEQUENCE: 2

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Thr Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255
```

```
Gly Leu Ala Phe Arg Val Phe His Cys Thr Gln Tyr Ile Arg His Gly
            260                 265                 270
Ser Lys Pro Met Tyr Thr Pro Glu Pro Asp Ile Cys His Glu Leu Leu
            275                 280                 285
Gly His Val Pro Leu Phe Ser Asp Arg Ser Phe Ala Gln Phe Ser Gln
            290                 295                 300
Glu Ile Gly Leu Ala Ser Leu Gly Ala Pro Asp Glu Tyr Ile Glu Lys
305                 310                 315                 320
Leu Ala Thr Ile Tyr Trp Phe Thr Val Glu Phe Gly Leu Cys Lys Gln
            325                 330                 335
Gly Asp Ser Ile Lys Ala Tyr Gly Ala Gly Leu Leu Ser Ser Phe Gly
            340                 345                 350
Glu Leu Gln Tyr Cys Leu Ser Glu Lys Pro Lys Leu Leu Pro Leu Glu
            355                 360                 365
Leu Glu Lys Thr Ala Ile Gln Asn Tyr Thr Val Thr Glu Phe Gln Pro
            370                 375                 380
Leu Tyr Tyr Val Ala Glu Ser Phe Asn Asp Ala Lys Glu Lys Val Arg
385                 390                 395                 400
Asn Phe Ala Ala Thr Ile Pro Arg Pro Phe Ser Val Arg Tyr Asp Pro
            405                 410                 415
Tyr Thr Gln Arg Ile Glu Val Leu Asp Asn Thr Gln Gln Leu Lys Ile
            420                 425                 430
Leu Ala Asp Ser Ile Asn Ser Glu Ile Gly Ile Leu Cys Ser Ala Leu
            435                 440                 445
Gln Lys Ile Lys
            450

<210> SEQ ID NO 3
<211> LENGTH: 452
<212> TYPE: PRT
<213> ORGANISM: Homo sapiens

<400> SEQUENCE: 3

Met Ser Thr Ala Val Leu Glu Asn Pro Gly Leu Gly Arg Lys Leu Ser
1               5                   10                  15
Asp Phe Gly Gln Glu Thr Ser Tyr Ile Glu Asp Asn Cys Asn Gln Asn
            20                  25                  30
Gly Ala Ile Ser Leu Ile Phe Ser Leu Lys Glu Glu Val Gly Ala Leu
            35                  40                  45
Ala Lys Val Leu Arg Leu Phe Glu Glu Asn Asp Val Asn Leu Thr His
            50                  55                  60
Ile Glu Ser Ser Pro Ser Arg Leu Lys Lys Asp Glu Tyr Glu Phe Phe
65                  70                  75                  80
Thr His Leu Asp Lys Arg Ser Leu Pro Ala Leu Thr Asn Ile Ile Lys
            85                  90                  95
Ile Leu Arg His Asp Ile Gly Ala Thr Val His Glu Leu Ser Arg Asp
            100                 105                 110
Lys Lys Lys Asp Thr Val Pro Trp Phe Pro Arg Thr Ile Gln Glu Leu
            115                 120                 125
Asp Arg Phe Ala Asn Gln Ile Leu Ser Tyr Gly Ala Glu Leu Asp Ala
            130                 135                 140
Asp His Pro Gly Phe Lys Asp Pro Val Tyr Arg Ala Arg Arg Lys Gln
145                 150                 155                 160
Phe Ala Asp Ile Ala Tyr Asn Tyr Arg His Gly Gln Pro Ile Pro Arg
            165                 170                 175
```

```
Val Glu Tyr Met Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
            245                 250                 255

Gly Leu Ala Phe Arg Val Phe His Cys Thr Gln Tyr Ile Arg His Gly
        260                 265                 270

Ser Lys Pro Met Tyr Thr Pro Glu Pro Asp Ile Cys His Glu Leu Leu
    275                 280                 285

Gly His Val Pro Leu Phe Ser Asp Arg Ser Phe Ala Gln Phe Ser Gln
290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
            325                 330                 335

Gly Asp Ser Ile Lys Ala Tyr Gly Ala Gly Leu Leu Ser Ser Phe Gly
        340                 345                 350

Glu Leu Gln Tyr Cys Leu Ser Glu Lys Pro Lys Leu Leu Pro Leu Glu
    355                 360                 365

Leu Glu Lys Thr Ala Ile Gln Asn Tyr Thr Val Thr Glu Phe Gln Pro
370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
            405                 410                 415

Tyr Thr Gln Arg Ile Glu Val Leu Asp Asn Thr Gln Gln Leu Lys Ile
        420                 425                 430

Leu Ala Asp Ser Ile Asn Ser Glu Ile Gly Ile Leu Cys Ser Ala Leu
    435                 440                 445

Gln Lys Ile Lys
    450

<210> SEQ ID NO 4
<211> LENGTH: 452
<212> TYPE: PRT
<213> ORGANISM: Homo sapiens

<400> SEQUENCE: 4

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95
```

```
Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Trp Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450

<210> SEQ ID NO 5
<211> LENGTH: 452
<212> TYPE: PRT
<213> ORGANISM: Homo sapiens

<400> SEQUENCE: 5

Met Ser Thr Ala Val Leu Glu Asn Pro Gly Leu Gly Arg Lys Leu Ser
1               5                   10                  15
```

-continued

Asp Phe Gly Gln Glu Thr Ser Tyr Ile Glu Asp Asn Cys Asn Gln Asn
                20                  25                  30

Gly Ala Ile Ser Leu Ile Phe Ser Leu Lys Glu Val Gly Ala Leu
            35                  40                  45

Ala Lys Val Leu Arg Leu Phe Glu Glu Asn Asp Val Asn Leu Thr His
     50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
            195                 200                 205

Ile Phe Pro Leu Leu Glu Lys Tyr Cys Gly Phe His Glu Asp Asn Ile
210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
            245                 250                 255

Gly Leu Ala Phe Gln Val Phe His Cys Thr Gln Tyr Ile Arg His Gly
            260                 265                 270

Ser Lys Pro Met Tyr Thr Pro Glu Pro Asp Ile Cys His Glu Leu Leu
            275                 280                 285

Gly His Val Pro Leu Phe Ser Asp Arg Ser Phe Ala Gln Phe Ser Gln
            290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
            355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu

```
              435                 440                 445
Gln Lys Ile Lys
    450

<210> SEQ ID NO 6
<211> LENGTH: 38
<212> TYPE: DNA
<213> ORGANISM: Homo sapiens

<400> SEQUENCE: 6
gatgtaaacc tgacccacac tgaatctaga ccttctcg                              38

<210> SEQ ID NO 7
<211> LENGTH: 38
<212> TYPE: DNA
<213> ORGANISM: Homo sapiens

<400> SEQUENCE: 7
cgagaaggtc tagattcagt gtgggtcagg tttacatc                              38

<210> SEQ ID NO 8
<211> LENGTH: 41
<212> TYPE: DNA
<213> ORGANISM: Homo sapiens

<400> SEQUENCE: 8
cctgacccac attgaatcta gtccttctcg tttaaagaaa g                          41

<210> SEQ ID NO 9
<211> LENGTH: 41
<212> TYPE: DNA
<213> ORGANISM: Homo sapiens

<400> SEQUENCE: 9
ctttctttaa acgagaagga ctagattcaa tgtgggtcag g                          41

<210> SEQ ID NO 10
<211> LENGTH: 30
<212> TYPE: DNA
<213> ORGANISM: Homo sapiens

<400> SEQUENCE: 10
ctgctttcct cttgggattt cttgggtggc                                       30

<210> SEQ ID NO 11
<211> LENGTH: 30
<212> TYPE: DNA
<213> ORGANISM: Homo sapiens

<400> SEQUENCE: 11
gccacccaag aaatcccaag aggaaagcag                                       30

<210> SEQ ID NO 12
<211> LENGTH: 40
<212> TYPE: DNA
<213> ORGANISM: Homo sapiens

<400> SEQUENCE: 12
cttgggtggc ctggccttcc aagtcttcca ctgcacacag                            40

<210> SEQ ID NO 13
<211> LENGTH: 40
<212> TYPE: DNA
<213> ORGANISM: Homo sapiens
```

<400> SEQUENCE: 13
ctgtgtgcag tggaagactt ggaaggccag gccacccaag                    40

<210> SEQ ID NO 14
<211> LENGTH: 326
<212> TYPE: PRT
<213> ORGANISM: Homo sapiens

<400> SEQUENCE: 14

Gly Ala Thr Val His Glu Leu Ser Arg Asp Lys Lys Asp Thr Val
1               5                   10                  15

Pro Trp Phe Pro Arg Thr Ile Gln Glu Leu Asp Arg Phe Ala Asn Gln
            20                  25                  30

Ile Leu Ser Tyr Gly Ala Glu Leu Asp Ala Asp His Pro Gly Phe Lys
        35                  40                  45

Asp Pro Val Tyr Arg Ala Arg Arg Lys Gln Phe Ala Asp Ile Ala Tyr
    50                  55                  60

Asn Tyr Arg His Gly Gln Pro Ile Pro Arg Val Glu Tyr Met Glu Glu
65                  70                  75                  80

Glu Lys Lys Thr Trp Gly Thr Val Phe Lys Thr Leu Lys Ser Leu Tyr
                85                  90                  95

Lys Thr His Ala Cys Tyr Glu Tyr Asn His Ile Phe Pro Leu Leu Glu
            100                 105                 110

Lys Tyr Cys Gly Phe His Glu Asp Asn Ile Pro Gln Leu Glu Asp Val
        115                 120                 125

Ser Gln Phe Leu Gln Thr Cys Thr Gly Phe Arg Leu Arg Pro Val Ala
    130                 135                 140

Gly Leu Leu Ser Ser Arg Asp Phe Leu Gly Gly Leu Ala Phe Arg Val
145                 150                 155                 160

Phe His Cys Thr Gln Tyr Ile Arg His Gly Ser Lys Pro Met Tyr Thr
                165                 170                 175

Pro Glu Pro Asp Ile Cys His Glu Leu Leu Gly His Val Pro Leu Phe
            180                 185                 190

Ser Asp Arg Ser Phe Ala Gln Phe Ser Gln Glu Ile Gly Leu Ala Ser
        195                 200                 205

Leu Gly Ala Pro Asp Glu Tyr Ile Glu Lys Leu Ala Thr Ile Tyr Trp
    210                 215                 220

Phe Thr Val Glu Phe Gly Leu Cys Lys Gln Gly Asp Ser Ile Lys Ala
225                 230                 235                 240

Tyr Gly Ala Gly Leu Leu Ser Ser Phe Gly Glu Leu Gln Tyr Cys Leu
                245                 250                 255

Ser Glu Lys Pro Lys Leu Leu Pro Leu Glu Leu Glu Lys Thr Ala Ile
            260                 265                 270

Gln Asn Tyr Thr Val Thr Glu Phe Gln Pro Leu Tyr Tyr Val Ala Glu
        275                 280                 285

Ser Phe Asn Asp Ala Lys Glu Lys Val Arg Asn Phe Ala Ala Thr Ile
    290                 295                 300

Pro Arg Pro Phe Ser Val Arg Tyr Asp Pro Tyr Thr Gln Arg Ile Glu
305                 310                 315                 320

Val Leu Asp Asn Thr Gln
                325